US011064902B2

(12) United States Patent
Wallace et al.

(10) Patent No.: US 11,064,902 B2
(45) Date of Patent: Jul. 20, 2021

(54) SYSTEMS, METHODS, AND MEDIA FOR AUTOMATICALLY DIAGNOSING INTRADUCTAL PAPILLARY MUCINOUS NEOSPLASMS USING MULTI-MODAL MAGNETIC RESONANCE IMAGING DATA

(71) Applicants: Mayo Foundation for Medical Education and Research, Rochester, MN (US); University of Central Florida Research Foundation, Inc., Orlando, FL (US)

(72) Inventors: Michael B. Wallace, Jacksonville, FL (US); Candice Bolan, Jacksonville, FL (US); Ulas Bagci, Oviedo, FL (US); Rodney Duane LaLonde, III, Oviedo, FL (US)

(73) Assignees: Mayo Foundation for Medical Education and Research, Rochester, MN (US); University of Central Florida Research Foundation, Inc., Orlando, FL (US)

( * ) Notice: Subject to any disclaimer, the term of this patent is extended or adjusted under 35 U.S.C. 154(b) by 1 day.

(21) Appl. No.: 16/459,437

(22) Filed: Jul. 1, 2019

(65) Prior Publication Data
US 2020/0000362 A1 Jan. 2, 2020

Related U.S. Application Data

(60) Provisional application No. 62/691,973, filed on Jun. 29, 2018.

(51) Int. Cl.
*G06K 9/00* (2006.01)
*A61B 5/055* (2006.01)
(Continued)

(52) U.S. Cl.
CPC .......... *A61B 5/055* (2013.01); *G06N 3/0454* (2013.01); *G06N 20/00* (2019.01); *G06T 7/0012* (2013.01);
(Continued)

(58) Field of Classification Search
CPC combination set(s) only.
See application file for complete search history.

(56) References Cited

U.S. PATENT DOCUMENTS

| | | | |
|---|---|---|---|
| 2017/0249744 A1* | 8/2017 | Wang | G06T 7/136 |
| 2020/0226748 A1* | 7/2020 | Kaufman | G06K 9/6292 |
| 2020/0286614 A1* | 9/2020 | Do | G16H 30/40 |

OTHER PUBLICATIONS

"Cancer Facts & Figures," American Cancer Society, 2016.
(Continued)

*Primary Examiner* — Jose L Couso
(74) *Attorney, Agent, or Firm* — Quarles & Brady LLP

(57) ABSTRACT

In accordance with some embodiments, systems, methods, and media for automatically diagnosing IPMNs using multi-modal MRI data are provided. In some embodiments, a system comprises: an MRI scanner; and a processor programmed to: prompt a user to select a slice of T1 and T2 MRI data including the subject's pancreas; generate minimum and maximum intensity projections based consecutive slices of the T1 and T2 MRI data; provide the projections to an image recognition CNN, and receive feature vectors for each from a fully connected layer; perform a canonical correlation analysis to determine correlations between the feature vectors; and provide a resultant vector to an SVM that determines whether the subject's pancreas includes IPMNs based on a vector.

19 Claims, 18 Drawing Sheets

(51) Int. Cl.
  *G06N 3/04* (2006.01)
  *G06T 7/00* (2017.01)
  *G06N 20/00* (2019.01)
(52) U.S. Cl.
  CPC .............. *G06T 2207/20081* (2013.01); *G06T 2207/20084* (2013.01)

(56) References Cited

OTHER PUBLICATIONS

Carreira, J., et al. "Quo vadis, action recognition? a new model and the kinetics dataset." In proceedings of the IEEE Conference on Computer Vision and Pattern Recognition, pp. 6299-6308. (2017).
Chatfield, K. et al, "Return of the devil in the details: Delving deep into convolutional nets," arXiv preprint arXiv:1405.3531, 2014.
Chen, W., et al. "Classification of Pancreatic Cystic Neoplasms Based on Multimodality Images." In International Workshop on Machine Learning in Medical Imaging (pp. 161-169). Springer, Cham. (2018).
Fenton JJ, et al. "Computer-aided detection in mammography: downstream effect on diagnostic testing, ductal carcinoma in situ treatment, and costs." JAMA Intern Med 2014;174:2032-4.
Gazit, L. et al, "Quantification of CT Images for the Classification of High-and Low-Risk Pancreatic Cysts," in SPIE Medical Imaging. International Society for Optics and Photonics, 2017, pp. 101340X-101340X.
Goyal, P., et al. "Accurate, large minibatch sgd: Training imagenet in 1 hour." arXiv preprint arXiv:1706.02677 (2017).
Haghighat, M. et al, "Fully automatic face normalization and single sample face recognition in unconstrained environments," Expert Systems with Applications, vol. 47, pp. 23-34, 2016.
Hanania, A. N. et al, "Quantitative imaging to evaluate malignant potential of IPMNs," Oncotarget, vol. 7, No. 52, pp. 85776, 2016.
He, H. et al, "ADASYN: Adaptive synthetic sampling approach for imbalanced learning," in Neural Networks, 2008. IJCNN 2008. (IEEE World Congress on Computational Intelligence). IEEE International Joint Conference on. IEEE, 2008, pp. 1322-1328.
He, K. et al, "Deep residual learning for image recognition," in Proceedings of the IEEE conference on computer vision and pattern recognition, 2016, pp. 770-778.
Huang et al., "Densely connected convolutional neural networks," Proceedings of the IEEE conference on computer vision and pattern recognition, pp. 4700-4708 (2017).
Hussein S, et al. "Automatic Segmentation and Quantification of White and Brown Adipose Tissues from PET/CT Scans." IEEE Trans Med Imaging 2017;36:734-44.
Hussein, S., et al. "Deep Multi-Modal Classification of Intraductal Papillary Mucinous Neoplasms (IPMN) with Canonical Correlation Analysis." IEEE International Symposium on Biomedical Imaging. (2018).
Kang MJ, et al. "Revisiting the concept of lymph node metastases of pancreatic head cancer: number of metastatic lymph nodes and lymph node ratio according to N stage." Ann Surg Oncol 2014;21:1545-51.
Laffan TA, et al. "Prevalence of unsuspected pancreatic cysts on MDCT." AJR Am J Roentgenol 2008;191:802-7.
Lakhani P. "Deep Convolutional Neural Networks for Endotracheal Tube Position and X-ray Image Classification: Challenges and Opportunities." J Digit Imaging 2017;30:460-8.
Lee A, et al. "Evaluation of AGA and Fukuoka Guidelines for EUS and surgical resection of incidental pancreatic cysts." Endosc Int Open 2017;5:E116-E22.
Lee KS, et al. "Prevalence of incidental pancreatic cysts in the adult population on MR imaging." Am J Gastroenterol 2010;105:2079-84.
Lichtenstein DR, et al. "Mucin-secreting tumors of the pancreas." Gastrointest Endosc Clin N Am 1995;5:237-58.
MA GK, et al. "Comparing American Gastroenterological Association Pancreatic Cyst Management Guidelines with Fukuoka Consensus Guidelines as Predictors of Advanced Neoplasia in Patients with Suspected Pancreatic Cystic Neoplasms." J Am Coll Surg 2016;223:729-37 e1.
Matthaei, H. et al, "Cystic precursors to invasive pancreatic cancer," Nature Reviews Gastroenterology and Hepatology, vol. 8, No. 3, pp. 141-150, 2011.
Ohno E, et al. "Malignant transformation of branch duct-type intraductal papillary mucinous neoplasms of the pancreas based on contrast-enhanced endoscopic ultrasonography morphological changes: focus on malignant transformation of intraductal papillary mucinous neoplasm itself." Pancreas 2012;41:855-62.
Roth HR, et al. "A new 2.5D representation for lymph node detection using random sets of deep convolutional neural network observations." Med Image Comput Comput Assist Interv 2014;17:520-7.
Russakovsky, O., et al: "ImageNet LargeScale Visual Recognition Challenge." IJCV (2015).
Sadot, E et al., "Tumor-associated neutrophils and malignant progression in intraductal papillary mucinous neoplasms: an opportunity for identification of high-risk disease," Annals of surgery, vol. 262, No. 6, pp. 1102, 2015.
Sharma K, et al. "Automatic Segmentation of Kidneys using Deep Learning for Total Kidney Volume Quantification in Autosomal Dominant Polycystic Kidney Disease." Sci Rep 2017;7:2049.
Shi C. et al, "Intraductal papillary mucinous neoplasm," Human pathology, vol. 43, No. 1, pp. 1-16, 2012.
Sighinolfi M, et al. "Fukuoka and AGA Criteria Have Superior Diagnostic Accuracy for Advanced Cystic Neoplasms than Sendai Criteria." Dig Dis Sci 2017;62:626-32.
Szegedy et al., "Rethinking inception architecture for computer vision," Proceedings of the IEEE conference on computer vision and pattern recognition, pp. 2818-2826 (2016).
Tajbakhsh N, et al. "Convolutional Neural Networks for Medical Image Analysis: Full Training or Fine Tuning?" IEEE Trans Med Imaging 2016;35:1299-312.
Tanaka M, et al. "International consensus guidelines for management of intraductal papillary mucinous neoplasms and mucinous cystic neoplasms of the pancreas." Pancreatology 2006;6:17-32.
Tanaka M, et al. "Revisions of international consensus Fukuoka guidelines for the management of IPMN of the pancreas." Pancreatology 2017;17:738-53.
Tustison, N. J. et al, "N4ITK: Improved N3 bias correction," IEEE Transactions on Medical Imaging, vol. 29, No. 6, pp. 1310-1320, 2010.
Vege SS, et al, "Clinical Guidelines C, American Gastroenterology A. American gastroenterological association institute guideline on the diagnosis and management of asymptomatic neoplastic pancreatic cysts" Gastroenterology 2015;148:819-22.
Wang X, et al. "Searching for prostate cancer by fully automated magnetic resonance imaging classification: deep learning versus non-deep learning." Sci Rep 2017;7:15415.
Xu MM, et al. "Comparison of the diagnostic accuracy of three current guidelines for the evaluation of asymptomatic pancreatic cystic neoplasms." Medicine (Baltimore) 2017;96:e7900.
Yasaka K, et al. "Deep Learning with Convolutional Neural Network for Differentiation of Liver Masses at Dynamic Contrast-enhanced CT: A Preliminary Study." Radiology 2017:170706.

\* cited by examiner

TABLE 1 *Results for accuracy, sensitivity and specificity of the proposed multi-modal fusion approach in comparison with single modality and feature concatenation based approaches.*

| Methods | Accuracy (%) | Sensitivity (%) | Specificity (%) |
|---|---|---|---|
| T1 scan only | 83.52 | 88.28 | 55.0 |
| T2 scan only | 67.47 | 67.14 | 66.50 |
| Concat of T1 and T2 | 81.57 | 87.71 | 51.0 |
| Feature Fusion (Proposed) | 84.18 | 85.86 | 82.17 |

| TABLE 2 Demographics | Normal N=31 | Low-risk dysplasia N=48 | High-risk dysplasia N=20 | Adenocarcinoma N=40 | Total N=139 |
|---|---|---|---|---|---|
| Age years ±SD | 59.6 ±13.6 | 64.5 ±7.9 | 69.2 ±5.7 | 68.8 ±14.9 | 65.3 ±11.9 |
| Gender % male | 41.9% | 35.4% | 35.0% | 52.5% | 41.7% |
| Ethnicity | White 83.9% Afrc-Amr 9.7% Other 6.5% | White 81.2% Afrc-Amr 10.4% Other 8.4% | White 100% | White 97.5% Afrc-Amr 2.5% | White 89.2% Afrc-Amr 6.5% Other 4.3% |
| BMI Kg/m² ±SD | 29.7 ±7.1 | 25.3 ±3.7 | 28.2 ±4.3 | 25.1 ±3.5 | 26.5 ±4.8 |
| Alcohol use | 35.5% | 52.1% | 60.0% | 57.5% | 51.1% |
| Tobacco use | 54.8% | 62.5% | 45.0% | 65.0% | 59.0% |
| Acute pancreatitis % with positive history (mean episodes) | 3.2% (2.0) | 16.7% (1.9) | 60.0% (2.4) | 22.5% (2.8) | 21.6% (2.4) |
| Chronic pancreatitis % with findings on imaging | 0.0% | 8.3% | 15.0% | 15.0% | 9.4% |

FIG. 9

| TABLE 3 Imaging findings | | Normal N=31 | Low-risk dysplasia N=48 | High-risk dysplasia N=20 | Adenocarcinoma N=40 |
|---|---|---|---|---|---|
| MRI | | | | | |
| Number of lesions | 1 | - | 54.2% | 60.0% | 75.0% |
| | 2 | - | 14.6% | 10.0% | 5.0% |
| | ≥3 | - | 31.2% | 30.0% | 20.0% |
| Largest lesion size (cm) | | - | 22.6 ± 12.9 | 27.5 ± 21.6 | 27.8 ± 11.6 |
| Location | Head | - | 33.3% | 40.0% | 62.5% |
| | Body | - | 20.8% | 10.0% | 10.0% |
| | Tail | - | 6.2% | 5.0% | 12.5% |
| | Multiple areas | - | 39.7% | 45.0% | 15.0% |
| Pancreatic duct | 5-9mm | 6.5% | 27.1% | 40.0% | 47.5% |
| | ≥10mm | 0.0% | 10.42% | 20.0% | 12.5% |
| Area of enhancement | | 0.0% | 8.3% | 15.0% | 32.5% |
| Ductal relation | Main duct (IPMN-MD) | - | 22.9% | 55.0% | 45.0% |
| | Side branch (IPMN-BD) | - | 47.9% | 20.0% | 37.5% |
| | Mixed | - | 29.2% | 25.0% | 17.5% |
| Fukuoka | | | | | |
| IPMN-MD | | 0.0% | 22.9% | 55.0% | 45.0% |
| IPMN-BD high-risk stigmata | | 3.2% | 12.5% | 5.0% | 17.5% |
| IPMN-BD worrisome features | | 0.0% | 29.2% | 30.0% | 25.0% |
| No concerning features | | 96.8% | 35.4% | 10.0% | 12.5% |
| AGA high-risk features | | | | | |
| 3 | | 0.0% | 2.1% | 0.0% | 15.0% |
| 2 | | 0.0% | 4.2% | 20.0% | 12.5% |
| 1 | | 0.0% | 47.9% | 60.0% | 55.0% |
| 0 | | 100.0% | 45.8% | 20.0% | 17.5% |
| Deep learning protocol | | | | | |
| Normal | | 51.6% | 12.5% | 5.0% | 5.0% |
| Low grade lesion | | 38.7% | 58.3% | 10.0% | 25.0% |
| High grade lesion | | 9.7% | 29.2% | 85.0% | 70.0% |
| EUS | | | | | |
| Diagnostic EUS performed | | 0.0% | 97.9% | 90.0% | 80.0% |
| Fine needle aspiration performed | | 0.0% | 78.7% | 72.2% | 67.5% |

FIG. 10

TABLE 4 Diagnostic performance to identify high-grade dysplasia or cancer

| | AGA[a] | Fukuoka[b] | Deep learning |
|---|---|---|---|
| Classified correctly | 65.5% | 70.5% | 76.9% |
| Sensitivity | 25.0% | 61.7% | 75.0% |
| Specificity | 96.2% | 77.2% | 78.5% |
| PPV | 83.3% | 67.3% | 72.6% |
| NPV | 62.8% | 72.6% | 80.5% |
| Area under ROC[c] | 0.769 (0.697 - 0.842) | 0.775 (0.700 - 0.851) | 0.783 (0.711 - 0.854) |

FIG. 11

TABLE 5 Experimental Results for IPMN Diagnosis by Architecture

| Method | Pre (SEM)% | Rec (SEM)% | Acc (SEM)% |
|---|---|---|---|
| Hussein et al. | - | - | 64.67 (0.83) |
| *InceptINN* Whole-MRI | 74.51 (4.70) | 71.24 (4.39) | 73.38 (3.52) |
| *InceptINN* Pancreas-ROI | 71.68 (2.25) | 70.11 (1.33) | 72.32 (0.97) |
| *DenseINN* Pancreas-ROI | 78.20 (4.17) | 69.09 (2.97) | 73.43 (2.26) |

FIG. 16

TABLE 6 Experimental Results for IPMN Diagnosis by Fusion Technique

| Method | Early Fusion | | | Intermediate Fusion | | |
|---|---|---|---|---|---|---|
| | Pre % | Rec % | Acc % | Pre % | Rec % | Acc % |
| *InceptINN* Whole-MRI | 69.44 | 66.35 | 73.33 | 66.67 | 59.68 | 66.67 |
| *InceptINN* Pancreas-ROI | 79.29 | 80.48 | 78.57 | 70.77 | 69.66 | 75.00 |
| *DenseINN* Pancreas-ROI | 73.08 | 73.08 | 75.00 | 88.10 | 75.21 | 82.14 |

FIG. 17

TABLE 7 Experimental Results for IPMN Diagnosis by MRI Slices

| k slices | Whole-MRI | | | Pancreas-ROI | | |
|---|---|---|---|---|---|---|
| | Pre% | Rec% | Acc% | Pre% | Rec% | Acc% |
| $k=3$ | 57.22 | 56.83 | 60.00 | 82.83 | 83.76 | 85.71 |
| $k=5$ | 66.67 | 59.68 | 66.67 | 70.77 | 69.66 | 75.00 |
| $k=7$ | - | - | - | 85.45 | 81.91 | 82.14 |

FIG. 18

SYSTEMS, METHODS, AND MEDIA FOR AUTOMATICALLY DIAGNOSING INTRADUCTAL PAPILLARY MUCINOUS NEOPLASMS USING MULTI-MODAL MAGNETIC RESONANCE IMAGING DATA

CROSS-REFERENCE TO RELATED APPLICATIONS

This application claims the benefit of U.S. Provisional Patent Application No. 62/691,973, filed Jun. 29, 2018, which is hereby incorporated herein by reference in its entirety for all purposes.

STATEMENT REGARDING FEDERALLY SPONSORED RESEARCH

This invention was made with government support under CA015083 awarded by the National Institutes of Health. The government has certain rights in the invention.

BACKGROUND

Cancer is one of the main causes of death in the world, with a mortality rate of about 171 per 100,000 men and women per year (based on 2008-2012 deaths). Among all cancers, pancreatic cancer has the poorest prognosis, with a 5-year survival rate of just 7% in the United States. Intraductal Papillary Mucinous Neoplasms (IPMNs) are pancreatic epithelial neoplasms that are grossly visible (typically >10 millimeter) lesions composed of mucin-producing columnar cells. The lesions show papillary proliferation, cyst formation, and varying degrees of cellular atypia. IPMNs are found in 3-14% of the population, but many lesions are underidentified or underreported. They are radiographically identifiable precursors to pancreatic cancer, which if left untreated can progress into invasive cancer with around one-third of resected IPMNs found to be associated with invasive carcinoma.

IPMNs may involve the main pancreatic duct, the branch ducts, or both. In general, patients with only branch duct lesions are at lower risk of developing malignancy (approximately 20% at 10 years), while patients with IPMNs involving the main duct are at higher risk (approximately 70%). Other factors such as the size and presence of contrast enhancement are also associated with increasing malignancy risk. As a result, accurate diagnosis and characterization of these lesions is important to make appropriate treatment recommendations. For example, IPMN tumors can undergo malignant transformation (approximately 10% of IPMN-BD after five years), and timely diagnosis of these lesions and identification of high-risk features followed by surgical treatment can reduce pancreatic cancer mortality.

However, identifying features that can be used to predict the risk of high-grade dysplasia or pancreatic adenocarcinoma is challenging. The American Gastroenterological Association (AGA) and the Fukuoka guidelines are radiographic criteria that are used by physicians to guide the treatment of IPMN when identified in abdominal magnetic resonance imaging (MRI).

Accordingly, systems, methods, and media for automatically diagnosing intraductal papillary mucinous neoplasms using multi-modal magnetic resonance imaging data are desirable.

SUMMARY

In accordance with some embodiments of the disclosed subject matter, systems, methods, and media for automatically diagnosing intraductal papillary mucinous neoplasms using multi-modal magnetic resonance imaging data are provided.

In accordance with some embodiments of the disclosed subject matter, a system for automatically detecting the presence of IPMNs in a subject's pancreas is provided, the system comprising: at least one hardware processor that is programmed to: receive T1 MRI data generated by an MRI machine, the T1 MRI data comprising a plurality of slices of T1 MRI data $[I_1, \ldots, I_u, \ldots, I_{N_1}]$; receive T2 MRI data generated by the MRI machine, the T2 MRI data comprising a plurality of slices of T2 MRI data $[J_1, \ldots, J_v, \ldots, J_{N_2}]$; provide data representing k slices of the T1 MRI data to a trained image classification convolutional neural network (CNN); provide data representing k slices of the T2 MRI data to the trained image classification CNN; receive output from the trained image classification CNN; determine, based on the output, that IPMNs are likely present in the subject's pancreas; in response to determining that IPMNs are likely present in the subject's pancreas, cause an indication that IPMNs are likely present in the subject's pancreas to be presented to the user In some embodiments, the system further comprises the MRI scanner.

In some embodiments, the at least one hardware processor that is further programmed to: present the T1 MRI data and prompt a user to select a slice of T1 MRI data including the subject's pancreas; and receive a selection of slice $I_u$ of the T1 MRI data.

In some embodiments, the at least one hardware processor is further programmed to: generate a minimum intensity projection based on consecutive slices $[I_{u-m}, \ldots, I_u, \ldots, I_{u+m}]$, where m is greater than or equal to 2, and the data representing the k slices of the T1 MRI data comprises the minimum intensity projection; generate a maximum intensity projection based on consecutive slices $[J_{v-m}, \ldots, J_v, \ldots, J_{v+m}]$, where m is greater than or equal to 2, and the data representing the k slices of the T2 MRI data comprises the maximum intensity projection; provide the minimum intensity projection to the image classification CNN; receive, from a fully connected layer of the image classification CNN, the output comprising a set of features $\Phi$ generated by the image classification CNN based on the minimum intensity projection; provide the maximum intensity projection to the CNN; receive, from the fully connected layer of the image classification CNN, a set of features $\Psi$ generated by the image classification CNN based on the maximum intensity projection; calculate a feature matrix based on a canonical correlation analysis (CCA) between features $\Phi$ and features $\Psi$; provide the feature matrix as input to a support vector machine (SVM) trained to automatically detect the presence of IPMNs in multi-modal MRI data corresponding to an imaged pancreas based on an input feature matrix generated from T1 and T2 MRI data corresponding to the imaged pancreas; receive an output from the SVM that is indicative of the presence of IPMNs in slice $I_u$ and slice $J_v$; and determine, based on the output from the SVM, that IPMNs are likely present in the subject's pancreas.

In some embodiments, the at least one hardware processor is further programmed to: provide the k slices of the T1 MRI data to the trained image classification CNN, wherein the trained image classification CNN was generated using transfer learning to retrain at least one layer of a 3D image classification CNN that was expanded from a pre-trained general image classification CNN having a 2D architecture, the data representing the k slices of the T1 MRI data comprising the k slices of the T1 MRI data, and the weights of a plurality of kernels of the trained classification CNN are divided at least by a number of depth layers d added to the 2D architecture that is equal to k; provide the k slices of the T2 MRI data to the trained image classification CNN; and receive the output from the trained image classification CNN.

In some embodiments, the at least one hardware processor is further programmed to: concatenate the T1 MRI data and the T2 MRI data prior to providing the T1 MRI data and the T2 MRI data to the trained image classification CNN.

In some embodiments, the at least one hardware processor is further programmed to: provide the k slices of the T1 MRI data to a first convolutional layer of the trained image classification CNN; provide the k slices of the T2 MRI data to a second convolutional layer of the trained image classification CNN; concatenate an output of the first convolutional layer and an output of the second convolution layer; and provide a set of features based on the concatenated outputs to a third convolutional layer.

In accordance with some embodiments of the disclosed subject matter, a method for automatically detecting the presence of IPMNs in a subject's pancreas is provided, the method comprising: receiving T1 MRI data generated by an MRI machine, the T1 MRI data comprising a plurality of slices of T1 MRI data $[I_1, \ldots, I_u, \ldots, I_{N_1}]$; receiving T2 MRI data generated by the MRI machine, the T2 MRI data comprising a plurality of slices of T2 MRI data $[J_1, \ldots, J_v, \ldots, J_{N_2}]$; providing data representing k slices of the T1 MRI data to a trained image classification convolutional neural network (CNN); providing data representing k slices of the T2 MRI data to the trained image classification CNN; receiving output from the trained image classification CNN; determining, based on the output, that IPMNs are likely present in the subject's pancreas; and in response to determining that IPMNs are likely present in the subject's pancreas, causing an indication that IPMNs are likely present in the subject's pancreas to be presented to the user.

In accordance with some embodiments of the disclosed subject matter, a non-transitory computer readable medium containing computer executable instructions that, when executed by a processor, cause the processor to perform a method for automatically detecting the presence of intraductal papillary mucinous neoplasms (IPMNs) in a subject's pancreas is provided, the method comprising: receiving T1 MRI data generated by an MRI machine, the T1 MRI data comprising a plurality of slices of T1 MRI data $[I_1, \ldots, I_u, \ldots, I_{N_1}]$; receiving T2 MRI data generated by the MRI machine, the T2 MRI data comprising a plurality of slices of T2 MRI data $[J_1, \ldots, J_v, \ldots, J_{N_2}]$; providing data representing k slices of the T1 MRI data to a trained image classification convolutional neural network (CNN); providing data representing k slices of the T2 MRI data to the trained image classification CNN; receiving output from the trained image classification CNN; determining, based on the output, that IPMNs are likely present in the subject's pancreas; and in response to determining that IPMNs are likely present in the subject's pancreas, causing an indication that IPMNs are likely present in the subject's pancreas to be presented to the user.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

FIG. 9 shows an example of a table showing demographics of subject's depicted in multi-modal MRI data used to train and evaluate a system for automatically diagnosing intraductal papillary mucinous neoplasms using multi-modal magnetic resonance imaging data implemented in accordance with some embodiments of the disclosed subject matter.

FIG. 10 shows an example of a table showing manually determined features present in the multi-modal magnetic resonance imaging data used to train and evaluate a system for automatically diagnosing intraductal papillary mucinous neoplasms using multi-modal magnetic resonance imaging data implemented in accordance with some embodiments of the disclosed subject matter, and performance of the system.

FIG. 11 shows an example of a table showing a comparison of the performance of conventional techniques and a system for automatically diagnosing intraductal papillary mucinous neoplasms using multi-modal magnetic resonance imaging data implemented in accordance with some embodiments of the disclosed subject matter.

FIG. 16 shows an example of a table of results comparing the precision, recall, and accuracy of a conventional technique for diagnosing IPMNs and various implementations of a system for automatically diagnosing IPMNs using multi-modal magnetic resonance imaging data in accordance with some embodiments of the disclosed subject matter.

FIG. 17 shows an example of a table of results comparing the precision, recall, and accuracy of various implementations of a system for automatically diagnosing IPMNs using multi-modal magnetic resonance imaging data using different fusion strategies in accordance with some embodiments of the disclosed subject matter.

FIG. 18 shows an example of a table of results comparing the precision, recall, and accuracy of a system for automatically diagnosing IPMNs using multi-modal MRI data using different regions of interest and different numbers of MRI slices in accordance with some embodiments of the disclosed subject matter.

DETAILED DESCRIPTION

In accordance with various embodiments, mechanisms (which can, for example, include systems, methods, and media) for using multi-modal magnetic resonance imaging data in the automatic diagnoses of intraductal papillary mucinous neoplasms (IPMNs) are provided.

Figure 1:
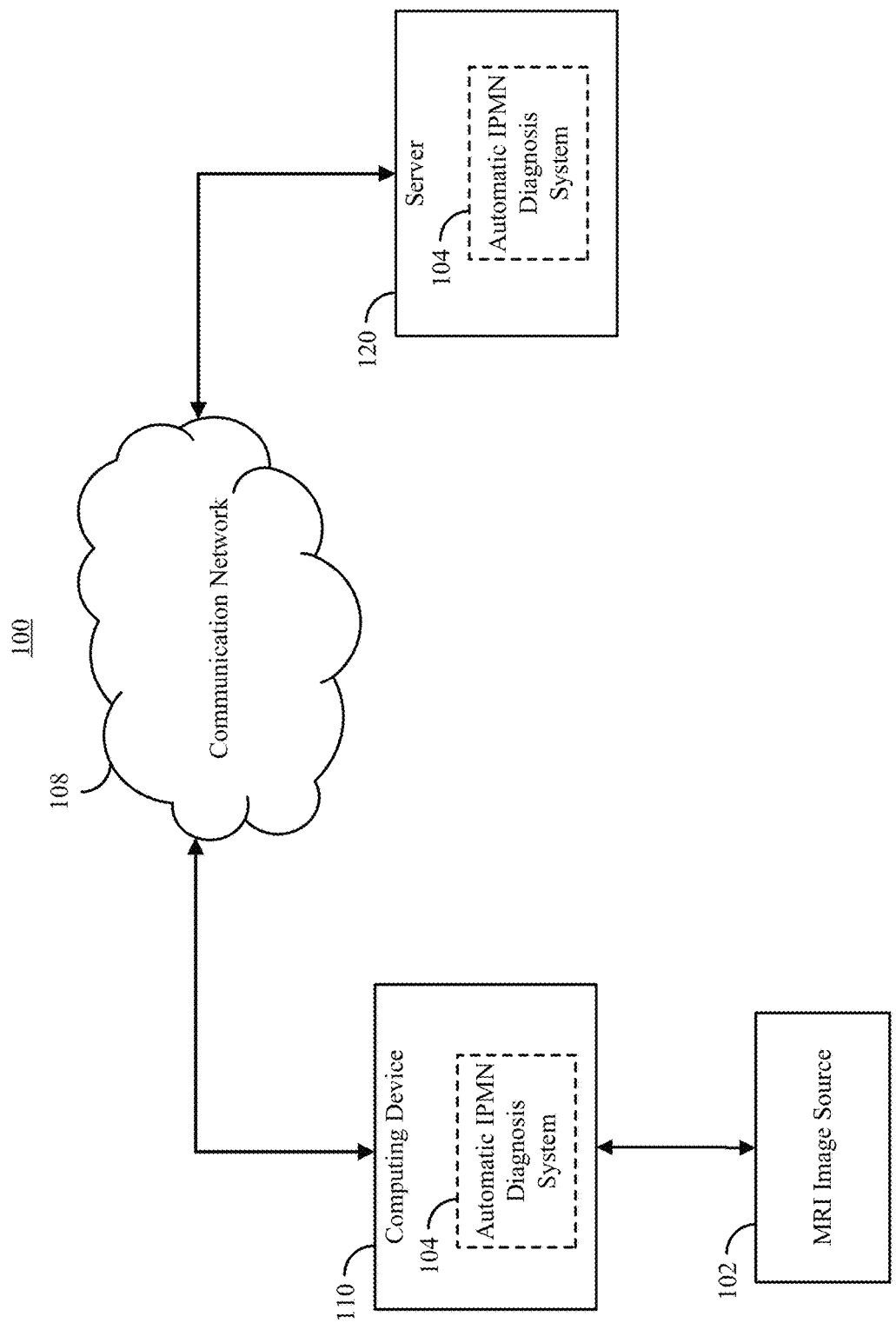
FIG. 1 shows an example of a system for automatically diagnosing intraductal papillary mucinous neoplasms using multi-modal magnetic resonance imaging data in accordance with some embodiments of the disclosed subject matter.

FIG. 1 shows an example 100 of a system for automatically diagnosing IPMNs using multi-modal MRI data in accordance with some embodiments of the disclosed subject matter. As shown in FIG. 1, a computing device 110 can receive multiple types of MRI data from MRI image source 102. In some embodiments, computing device 110 can execute at least a portion of an automatic IPMN diagnosis system 104 to automatically determine whether IPMNs are present in MRI images of a subject's pancreas based on information from both T1 MRI data and T2 MRI data corresponding to the subject's pancreas.

Additionally or alternatively, in some embodiments, computing device 110 can communicate information about MRI data received from MRI image source 102 to a server 120 over a communication network 108, which can execute at least a portion of automatic IPMN diagnosis system 104 to automatically determine whether IPMNs are present in MRI images of a subject's pancreas based on information from both T1 MRI data and T2 MRI data corresponding to the subject's pancreas. In such embodiments, server 120 can return information to computing device 110 (and/or any other suitable computing device) indicative of an output of automatic IPMN diagnosis system 104 to determine whether IPMNs are present or absent.

In some embodiments, computing device 110 and/or server 120 can be any suitable computing device or combination of devices, such as a desktop computer, a laptop computer, a smartphone, a tablet computer, a wearable computer, a server computer, a virtual machine being executed by a physical computing device, etc. As described below in connection with FIGS. 3-6, in some embodiments, automatic IPMN diagnosis system 104 can extract features from labeled (e.g., labeled as including IPMNs or normal) T1 and T2 MRI data, respectively, using a convolutional neural network (CNN) trained as a general image classifier, and can perform a Canonical Correlation Analysis (CCA) to calculate correlations between the features corresponding to the T1 MRI data, and the features corresponding to the T2 MRI data. In some embodiments, the CCA features calculated for various pairs of the labeled T1 and T2 MRI data can be used to train a classification model, such as a support vector machine (SVM), to classify CCA features as indicative of IPMNs or as indicative of a normal pancreas. In some embodiments, automatic IPMN diagnosis system 104 can provide CCA features for unlabeled T1 and T2 MRI data to the trained classification model and can present an IPMNs diagnosis based on the output of the classification model (e.g., based on which class the SVM identifies the CCA features with).

In some embodiments, MRI image source 102 can be any suitable source of MRI image data, such as an MRI machine, another computing device (e.g., a server storing MRI image data), etc. In some embodiments, MRI image source 102 can be local to computing device 110. For example, MRI image source 102 can be incorporated with computing device 110 (e.g., computing device 110 can be configured as part of a device for capturing and/or storing MRI images). As another example, MRI image source 102 can be connected to computing device 110 by a cable, a direct wireless link, etc. Additionally or alternatively, in some embodiments, MRI image source 102 can be located locally and/or remotely from computing device 110, and can communicate MRI image data to computing device 110 (and/or server 120) via a communication network (e.g., communication network 108).

In some embodiments, communication network 108 can be any suitable communication network or combination of communication networks. For example, communication network 108 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, etc. In some embodiments, communication network 108 can be a local area network, a wide area network, a public network (e.g., the Internet), a private or semi-private network (e.g., a corporate or university intranet), any other suitable type of network, or any suitable combination of networks. Communications links shown in FIG. 1 can each be any suitable communications link or combination of communications links, such as wired links, fiber optic links, Wi-Fi links, Bluetooth links, cellular links, etc.

Figure 2:
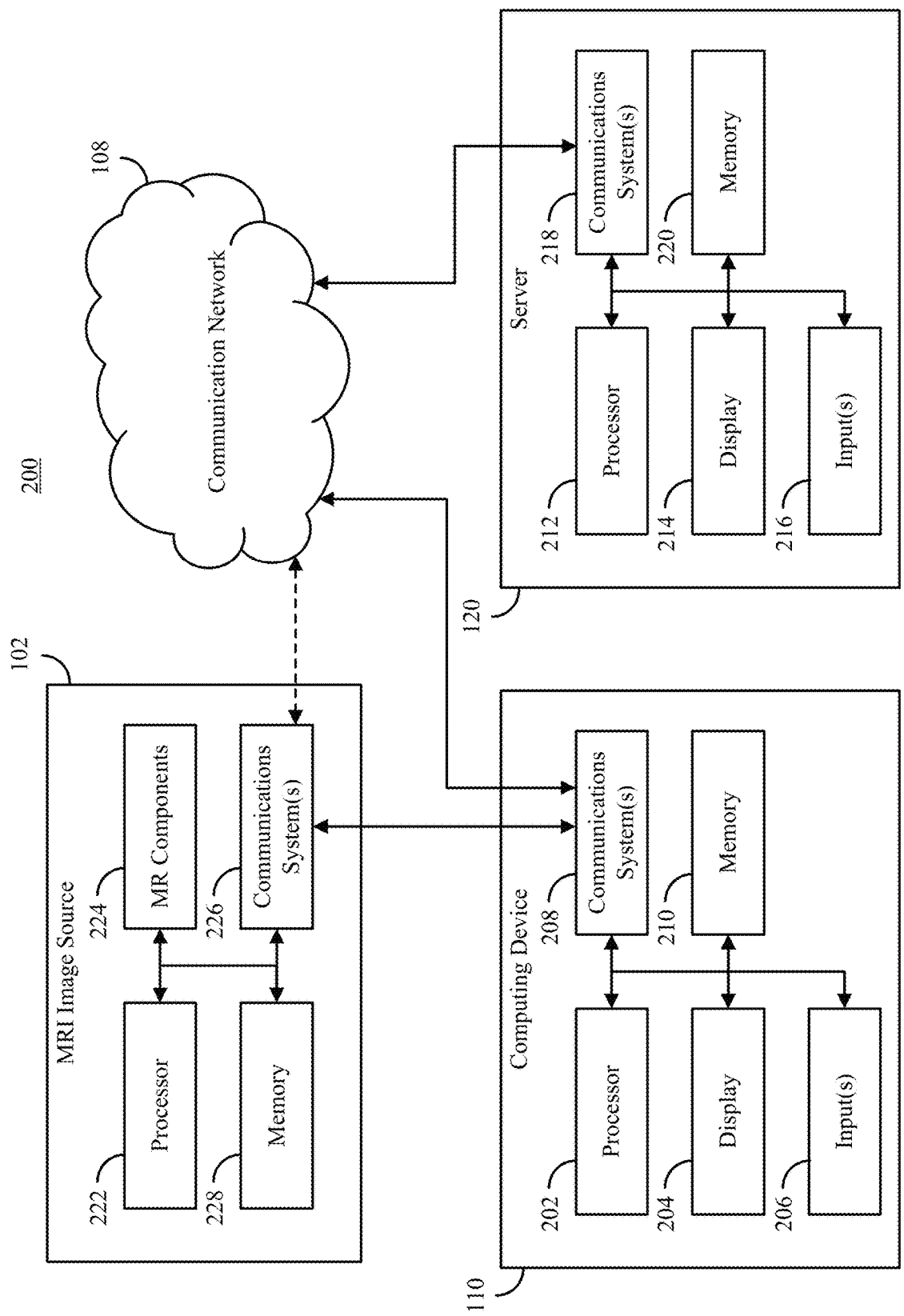
FIG. 2 shows an example of hardware that can be used to implement a magnetic resonance imaging image source, a computing device, and a server, shown in FIG. 1 in accordance with some embodiments of the disclosed subject matter.

FIG. 2 shows an example 200 of hardware that can be used to implement MRI image source 102, computing device 110, and/or server 120 in accordance with some embodiments of the disclosed subject matter. As shown in FIG. 2, in some embodiments, computing device 110 can include a processor 202, a display 204, one or more inputs 206, one or more communication systems 208, and/or memory 210. In some embodiments, processor 202 can be any suitable hardware processor or combination of processors, such as a central processing unit (CPU), a graphics processing unit (GPU), etc. In some embodiments, display 204 can include any suitable display devices, such as a computer monitor, a touchscreen, a television, etc. In some embodiments, inputs 206 can include any suitable input devices and/or sensors that can be used to receive user input, such as a keyboard, a mouse, a touchscreen, a microphone, etc.

In some embodiments, communications systems 208 can include any suitable hardware, firmware, and/or software for communicating information over communication network 108 and/or any other suitable communication networks. For example, communications systems 208 can include one or more transceivers, one or more communication chips and/or chip sets, etc. In a more particular example, communications systems 208 can include hardware, firmware and/or software that can be used to establish a Wi-Fi connection, a Bluetooth connection, a cellular connection, an Ethernet connection, etc.

In some embodiments, memory 210 can include any suitable storage device or devices that can be used to store instructions, values, etc., that can be used, for example, by processor 202 to present content using display 204, to communicate with server 120 via communications system(s) 208, etc. Memory 210 can include any suitable volatile memory, non-volatile memory, storage, or any suitable combination thereof. For example, memory 210 can include RAM, ROM, EEPROM, one or more flash drives, one or more hard disks, one or more solid state drives, one or more optical drives, etc. In some embodiments, memory 210 can have encoded thereon a computer program for controlling operation of computing device 110. In such embodiments, processor 202 can execute at least a portion of the computer program to present content (e.g., MRI images, user interfaces, graphics, tables, etc.), receive content from server 120, transmit information to server 120, etc.

In some embodiments, server 120 can include a processor 212, a display 214, one or more inputs 216, one or more communications systems 218, and/or memory 220. In some embodiments, processor 212 can be any suitable hardware processor or combination of processors, such as a CPU, a GPU, etc. In some embodiments, display 214 can include any suitable display devices, such as a computer monitor, a touchscreen, a television, etc. In some embodiments, inputs 216 can include any suitable input devices and/or sensors that can be used to receive user input, such as a keyboard, a mouse, a touchscreen, a microphone, etc.

In some embodiments, communications systems 218 can include any suitable hardware, firmware, and/or software for communicating information over communication network 108 and/or any other suitable communication networks. For example, communications systems 218 can include one or more transceivers, one or more communication chips and/or chip sets, etc. In a more particular example, communications systems 218 can include hardware, firmware and/or software that can be used to establish a Wi-Fi connection, a Bluetooth connection, a cellular connection, an Ethernet connection, etc.

In some embodiments, memory 220 can include any suitable storage device or devices that can be used to store instructions, values, etc., that can be used, for example, by processor 212 to present content using display 214, to communicate with one or more computing devices 110, etc. Memory 220 can include any suitable volatile memory, non-volatile memory, storage, or any suitable combination thereof. For example, memory 220 can include RAM, ROM, EEPROM, one or more flash drives, one or more hard disks, one or more solid state drives, one or more optical drives, etc. In some embodiments, memory 220 can have encoded thereon a server program for controlling operation of server 120. In such embodiments, processor 212 can execute at least a portion of the server program to transmit information and/or content (e.g., MRI data, results of automatic IPMN diagnosis, a user interface, etc.) to one or more computing devices 110, receive information and/or content from one or more computing devices 110, receive instructions from one or more devices (e.g., a personal computer, a laptop computer, a tablet computer, a smartphone, etc.), etc.

In some embodiments, MRI image source 102 can include a processor 222, magnetic resonance (MR) components 224, one or more communications systems 226, and/or memory 228. In some embodiments, processor 222 can be any suitable hardware processor or combination of processors, such as a CPU, a GPU, etc. In some embodiments, MR components 224 can be any suitable components to generate MRI data corresponding to one or more MRI imaging modes (e.g., T1 imaging, T2 imaging, fMRI, etc.). An example of an MRI machine that can be used to implement MRI image source 102 can include a conventional MRI scanner (e.g., a 1.5 T scanner, a 3 T scanner), a high field MRI scanner (e.g., a 7 T scanner), an open bore MRI scanner, etc.

Note that, although not shown, MRI image source 102 can include any suitable inputs and/or outputs. For example, MRI image source 102 can include input devices and/or sensors that can be used to receive user input, such as a keyboard, a mouse, a touchscreen, a microphone, a trackpad, a trackball, hardware buttons, software buttons, etc. As another example, MRI image source 102 can include any suitable display devices, such as a computer monitor, a touchscreen, a television, etc., one or more speakers, etc.

In some embodiments, communications systems 226 can include any suitable hardware, firmware, and/or software for communicating information to computing device 110 (and, in some embodiments, over communication network 108 and/or any other suitable communication networks). For example, communications systems 226 can include one or more transceivers, one or more communication chips and/or chip sets, etc. In a more particular example, communications systems 226 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, etc.

In some embodiments, memory 228 can include any suitable storage device or devices that can be used to store instructions, values, MRI data, etc., that can be used, for example, by processor 222 to: control MRI components 224, and/or receive MR data from MR components 224; generate MRI images; present content (e.g., MRI images, a user interface, etc.) using a display; communicate with one or more computing devices 110; etc. Memory 228 can include any suitable volatile memory, non-volatile memory, storage, or any suitable combination thereof. For example, memory 228 can include RAM, ROM, EEPROM, one or more flash drives, one or more hard disks, one or more solid state drives, one or more optical drives, etc. In some embodiments, memory 228 can have encoded thereon a program for controlling operation of MRI image source 102. In such embodiments, processor 222 can execute at least a portion of the program to generate T1 MRI images and/or T2 MRI images, transmit information and/or content (e.g., MRI image data) to one or more computing devices 110, receive information and/or content from one or more computing devices 110, receive instructions from one or more devices (e.g., a personal computer, a laptop computer, a tablet computer, a smartphone, etc.), etc.

Figure 3:
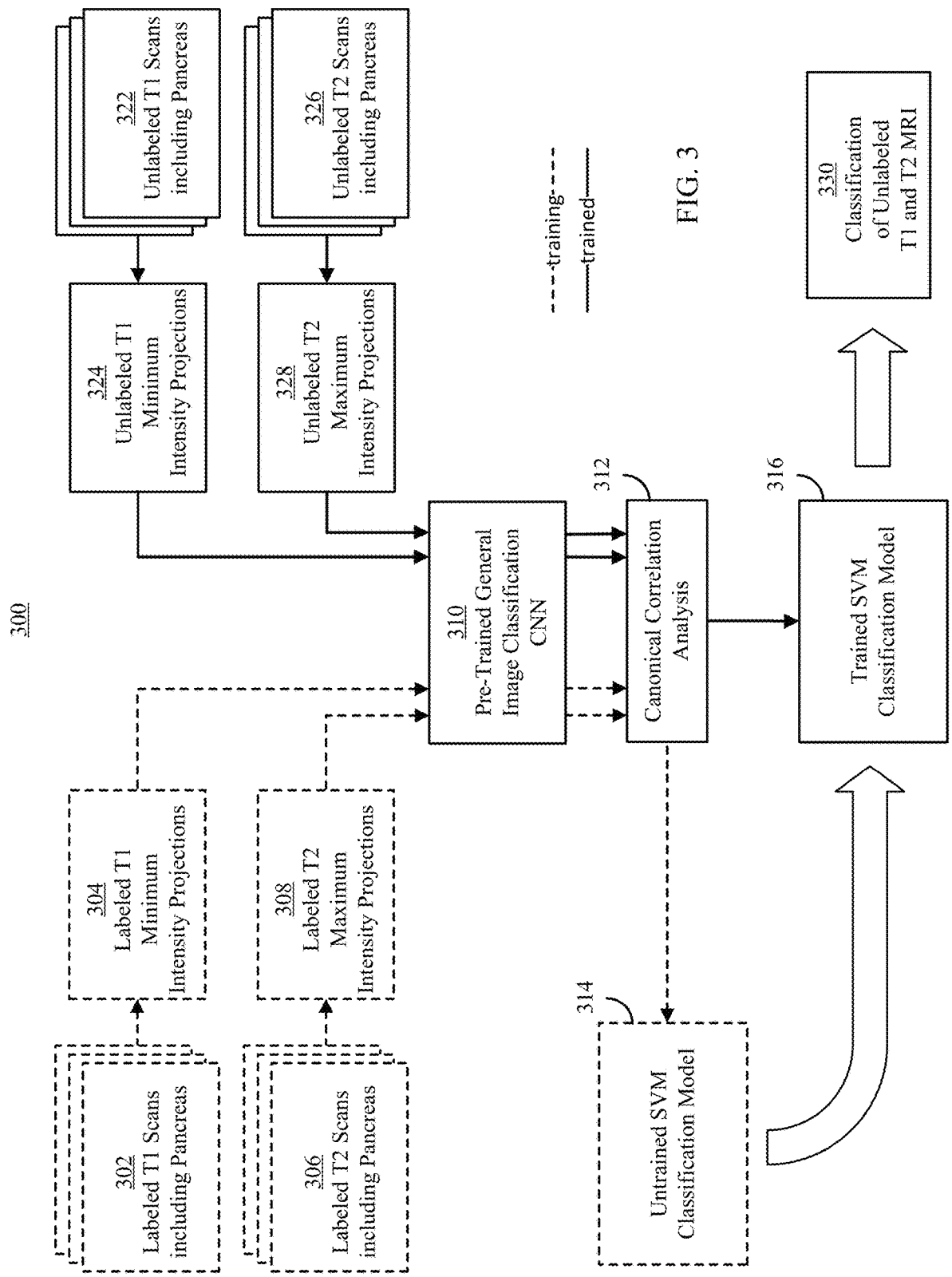
FIG. 3 shows an example of a flow for training and using mechanisms for automatically diagnosing intraductal papillary mucinous neoplasms using multi-modal magnetic resonance imaging data in accordance with some embodiments of the disclosed subject matter.

FIG. 3 shows an example 300 of a flow for training and using mechanisms for automatically diagnosing IPMN using multi-modal MRI data in accordance with some embodiments of the disclosed subject matter. As shown in FIG. 3, labeled examples 302 of T1 scans of a variety of subjects that include at least one image of the subject's pancreas can be used to generate training data, with each labeled T1 scan being labeled as corresponding to a "normal" pancreas (or a pancreas lacking IPMNs) or labeled as having IPMNs. For example, a user(s) (e.g., a physician) can select an image from each labeled T1 scan 302 that shows the subject's pancreas.

In some embodiments, using a single slice as training data may lead to overfitting to the training data, and may miss potentially important contextual information included in the other slices. Accordingly, in some embodiments, additional information can be introduced based on surrounding images. For example, because IPMNs and pancreatic cysts are hypo-intensity regions in T1, a labeled minimum intensity projection 304 can be generated for each scan by taking the minimum intensity value at each lateral (X-Y) location from among the selected image and neighboring images (e.g., from four neighboring images in the Z direction, two on each side).

Similarly, labeled examples 306 of T2 scans of the variety of subject's that include at least one image of the subject's pancreas can be used to generate additional training data. For example, a user(s) (e.g., a physician) can select an image from each labeled T2 scan 306 that shows the subject's pancreas, and a labeled maximum intensity projection 308 can be generated for each scan by taking the maximum intensity value at each lateral (X-Y) location from among the selected image and neighboring images (e.g., from four neighboring images in the Z direction, two on each side).

In some embodiments, each labeled minimum intensity projections 304 can be provided as input to a pre-trained general image recognition CNN 310. For example, the pre-trained CNN can be a CNN that was trained using examples from the ImageNet dataset to recognize a variety of objects and/or classify images. In a more particular example, pre-trained CNN 310 can be an instance of the fast CNN (CNN-F) described in Chatfield et al., "Return of the Devil in the Details: Delving Deep into Convolutional Nets," available at arxiv(dot)org, 2014, described in more detail below in connection with FIGS. 5A and 5B. For each labeled minimum intensity projection 304 pre-trained CNN 310 can produce a set of features. For example, the features can be the output of a fully connected layer of the CNN. Similarly, in some embodiments, each labeled maximum intensity projection 308 can be provided as input to pre-trained CNN 310 to produce a set of features In some embodiments, for each subject, a CCA can be performed using the features extracted from labeled minimum intensity projections 304 as one input matrix, and the features extracted from labeled maximum intensity projections 308 as the input matrix. A labeled feature matrix (described below in connection with FIG. 4B) produced by the CCA for each pair of T1 and T2 can be used as training data for a classification model, such as an untrained SVM 314, which can be trained using any suitable technique or combination of techniques to create a trained SVM 316.

In some embodiments, after training of trained SVM 316 is complete, a particular image (slice) of an unlabeled T1 scan 322 of a subject to be diagnosed can be selected, and used, with its neighbors to produce an unlabeled minimum intensity projection 324. Similarly, a particular image (slice) of an unlabeled T2 scan 326 of a subject to be diagnosed can be selected, and used, with its neighbors to produce an unlabeled maximum intensity projection 328.

In some embodiments, unlabeled minimum intensity projections 324 and unlabeled maximum intensity projections 328 can each be provided to pre-trained CNN 310 to produce features (e.g., from a fully connected layer of pre-trained CNN 310), which can then be used during a CCA to produce an unlabeled feature vector to use as input to trained SVM 316.

In some embodiments, trained SVM 316 can provide a classification 330 of the subject of the T1 and T2 scans that is indicative of the predicted presence of IPMNs. For example, the subject can be classified as having a "normal" pancreas, or as showing IPMNs. Note that although SVM 316 is described above as being used to classify the output of the canonical correlation analysis this is merely an example, and other classification models can be used.

Figure 4A:
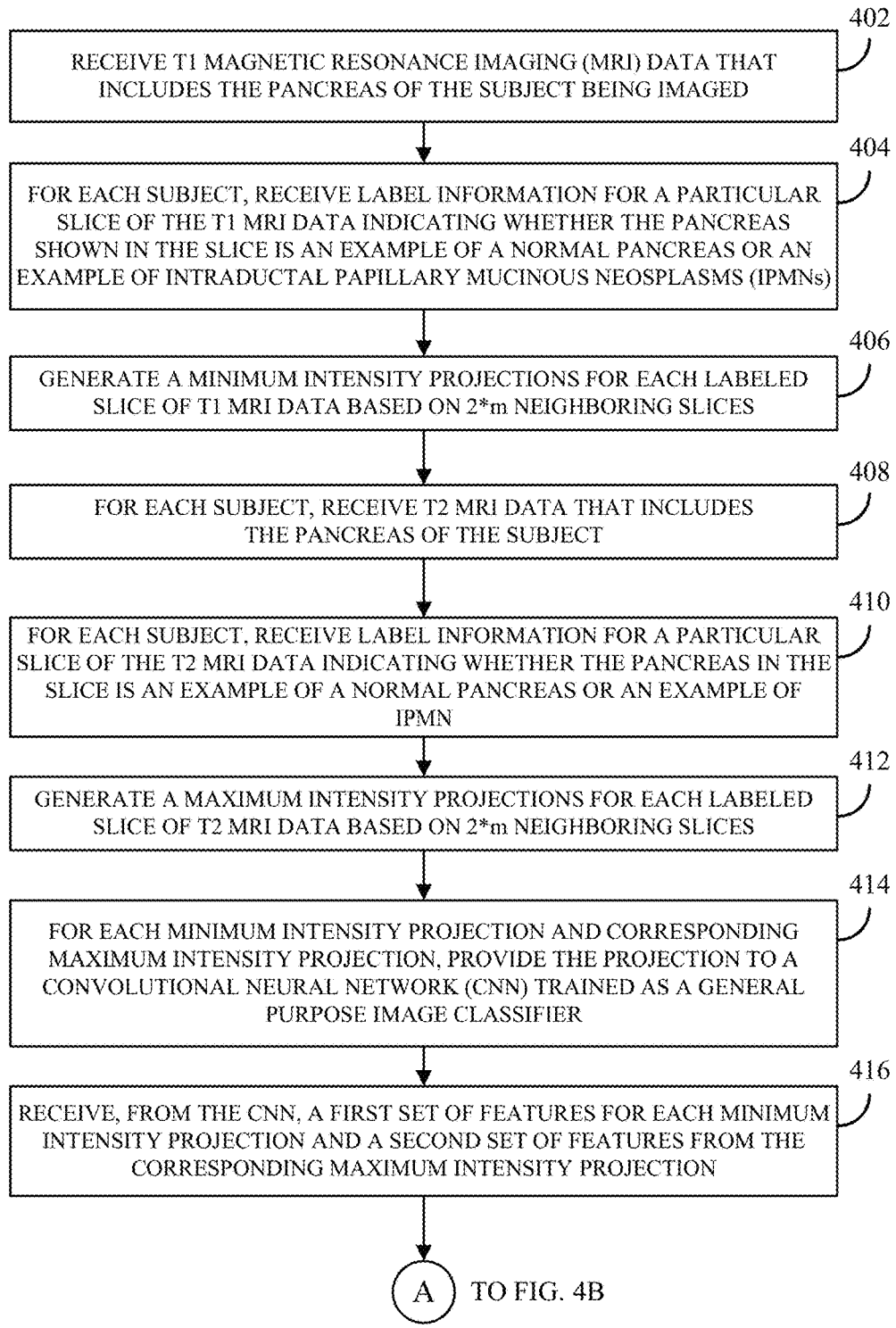
FIG. 4A shows an example of a portion of a process for training and using a system for automatically diagnosing intraductal papillary mucinous neoplasms using multi-modal magnetic resonance imaging data in accordance with some embodiments of the disclosed subject matter.
Figure 4B:
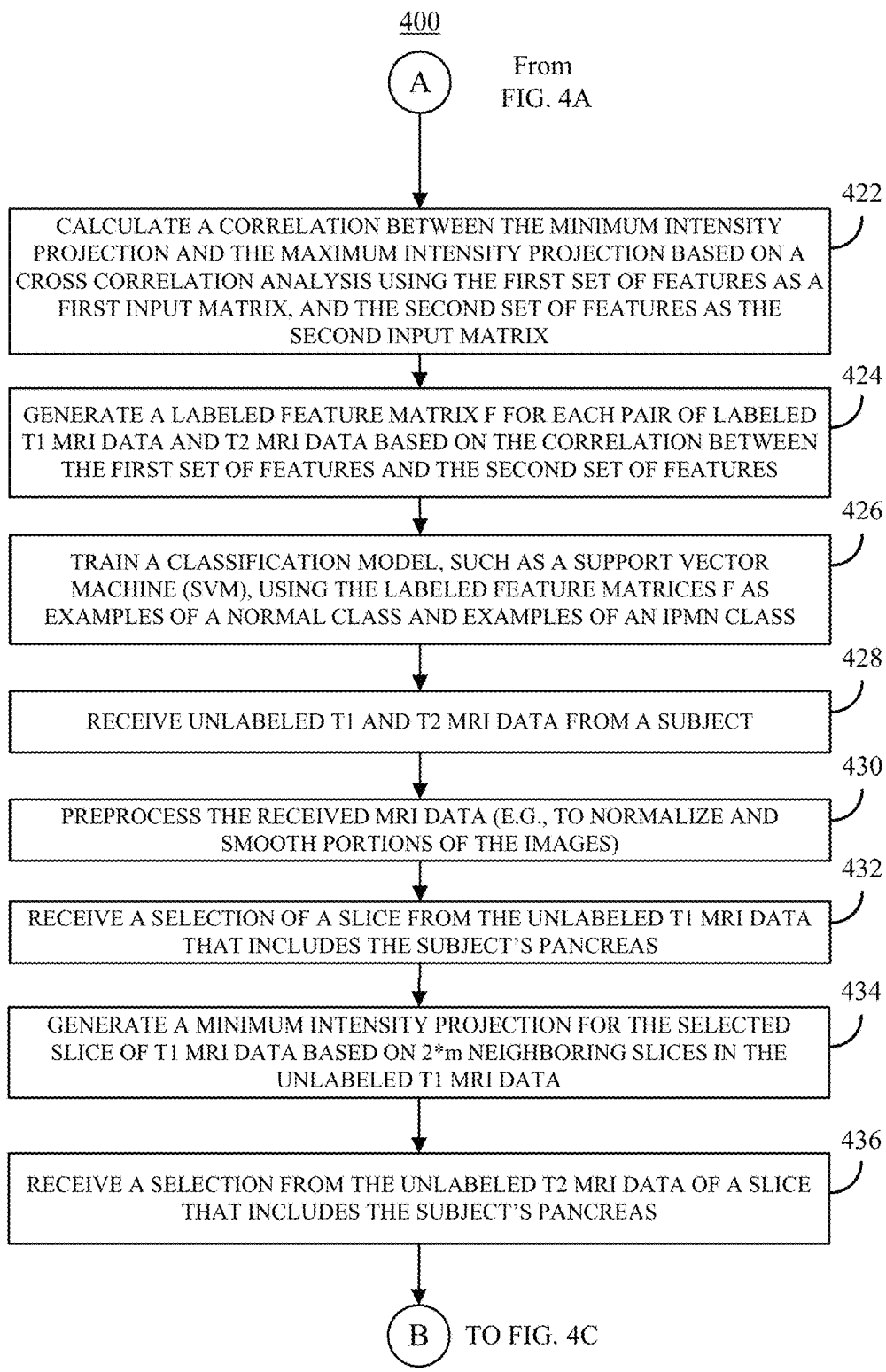
FIG. 4B shows an example of another portion of a process for training and using a system for automatically diagnosing intraductal papillary mucinous neoplasms using multi-modal magnetic resonance imaging data in accordance with some embodiments of the disclosed subject matter.
Figure 4C:
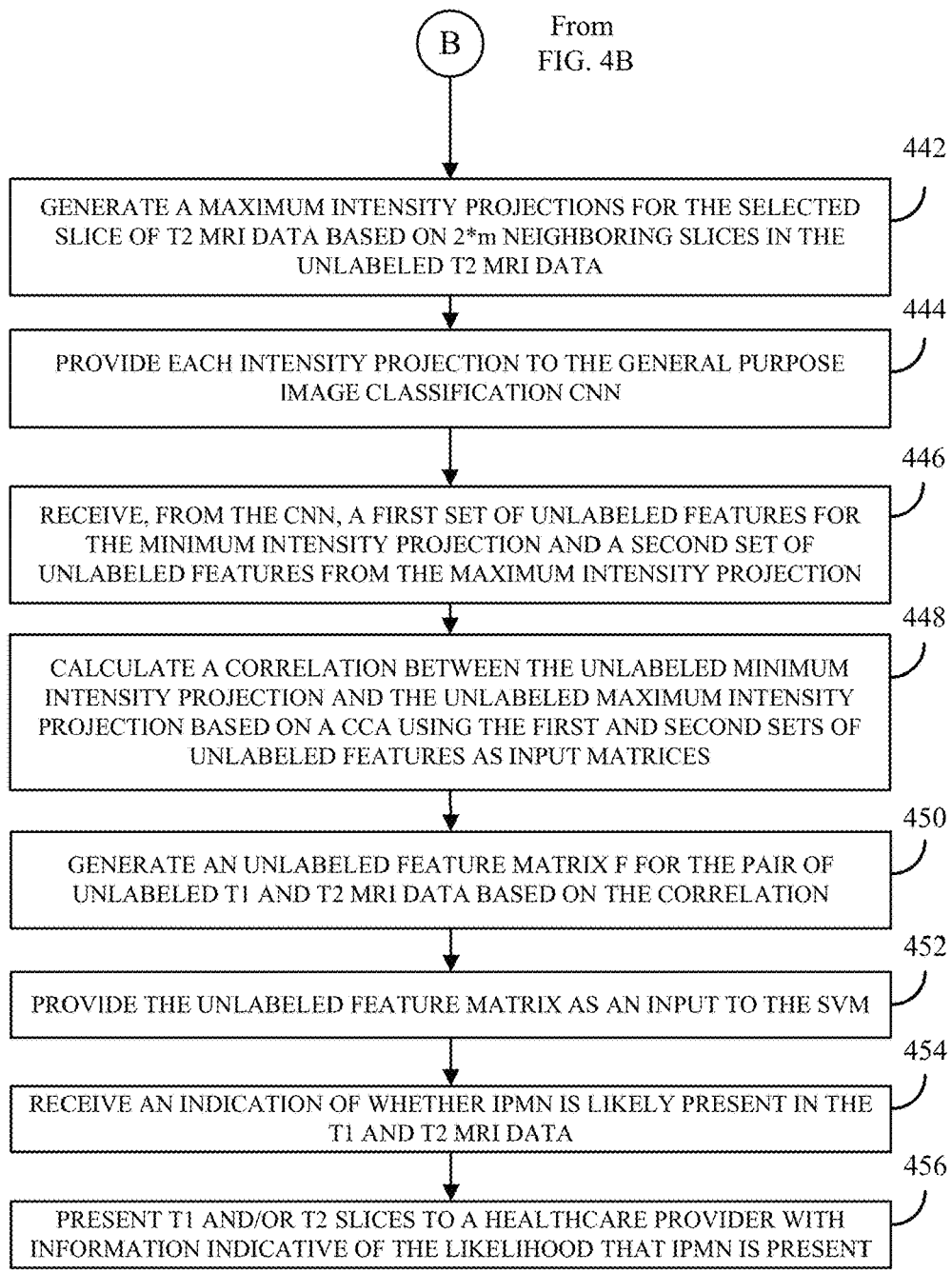
FIG. 4C shows an example of yet another portion of a process for training and using a system for automatically diagnosing intraductal papillary mucinous neoplasms using multi-modal magnetic resonance imaging data in accordance with some embodiments of the disclosed subject matter.

FIGS. 4A to 4C show an example 400 of a process for training and using a system for automatically diagnosing IPMN using multi-modal MRI data in accordance with some embodiments of the disclosed subject matter. As shown in FIG. 4A, process 400 can receive T1 MRI data that includes the pancreas of the subject being images. As described above in connection with FIG. 1, process 400 can receive the T1 MRI data from an MRI image source (e.g., MRI image source 102), another computing device (e.g., server 120), or a storage medium (e.g., an external hard drive).

At 404, process 400 can receive label information for each subject of the T1 MRI data indicating whether the subject's pancreas is normal or whether the subject's pancreas includes examples of IPMNs. Additionally, in some embodiments, process 400 can receive a selection of a particular image (e.g., a slice) of the T1 MRI data to be used as training data.

In some embodiments, process 400 can receive the label information and/or selection using any suitable technique or combination of techniques. For example, in some embodiments, process 400 can receive the labels and/or selection with the MRI data (e.g., as metadata). As another example, in some embodiments, process 400 can present at least a portion of the MRI data with a user interface that is configured to receive label information and/or a selection of a particular slice of the MRI data.

In some embodiments, the T1 MRI data can be preprocessed before, during, or after, reception of the label information and/or selection. For example, process 400 can include applying an N4 bias field correction to the T1 MRI data to normalize variations in image intensity. In such an example, N4 bias-field correction can be used to change the intensity values of pixels in the image (i.e., to correct the pixel values) prior to other processing (e.g., generating including minimum and maximum projections as described below in connection with 406 and 412). As another example, a curvature anisotropic image filter can be applied to the T1 MRI data to smooth the images while preserving edges.

At 406, process 400 can generate a minimum intensity projection based on the T1 MRI data and the selected slice of the T1 MRI data representing the subject's pancreas. In some embodiments, process 400 can use the intensity values from the selected slice and from m neighboring slices on each side of the selected slice. Process 400 can compare the intensity values at each X-Y position among the 2m+1 slices and can select the minimum intensity value at each position to generate the minimum intensity projection.

At 408, process 400 can receive T2 MRI data depicting the subjects of the T1 MRI data received at 402. Process 400 can receive the T2 image data using techniques similar to the techniques described above in connection with 402.

At 410, process 400 can receive label information for each subject of the T2 MRI data indicating whether the subject's pancreas is normal or whether the subject's pancreas includes examples of IPMNs. Additionally, in some embodiments, process 400 can receive a selection of a particular image (sometimes referred to as a slice) of the T2 MRI data to be used as training data. In some embodiments, the label information can be the same label information received at 404 (e.g., the T1 and T2 MRI data for a subject can be associated with the same label information). In some embodiments, the selection of a particular slice can be made using techniques similar to the techniques described above for selecting a slice of T1 MRI data in connection with 404. Additionally, in some embodiments, the selection of the T2 MRI slice can be made simultaneously with the selection of the T1 MRI slice (e.g., the slices from each can be correlated and presented side-by-side for selection). In some embodiments, the T2 MRI slice that is selected can correspond to the same portion of the subject's pancreas (e.g., the same cross section of the pancreas). Alternatively, in some embodiments, the T2 MRI slice and the T1 MRI slice can be selected independently and may correspond to different portions of the pancreas.

At 412, process 400 can generate a maximum intensity projection based on the T2 MRI data and the selected slice of the T2 MRI data representing the subject's pancreas. In some embodiments, process 400 can use the intensity values from the selected slice and from m neighboring slices on each side of the selected slice. Process 400 can compare the intensity values at each X-Y position among the 2m+1 slices, and can select the maximum intensity value at each position to generate the maximum intensity projection.

More generally, the T1 MRI data received at 402 for a particular subject can be represented as $I_{T1}=[I_1, I_2, \ldots, I_{N_1}]\in \mathbb{R}^{X_1 \times Y_1 \times N_1}$, where the subscript represents a slice of the scan. Similarly, the T2 MRI data received at 408 for a particular subject can be represented as $J_{T2}=[J_1, J_2, \ldots, J_{N_2}]\in \mathbb{R}^{X_1 \times Y_1 \times N_2}$. For example, $I_u$ can represent the slice selected from the T1 MRI scan at 404 that includes the pancreas, and $J_v$ can represent the slice selected from the T2 MRI scan at 410 that includes the pancreas. In general, corresponding slices $I_u$ and $J_v$ depict the same part of the subject's anatomy, as the T1 and T2 images are typically aligned with one another. As described above in connection with FIG. 3, predicting the label from a single slice may cause the classification model to be overfitted to the labeled slices, and may miss important contextual information from other slices. Generating the minimum and maximum intensity projections (at 406 and 412, respectively) can include including sampling k=2 consecutive slices before and after $I_u$ and $J_v$ in $I_{T1}$ and $J_{T2}$, respectively. Due to the CNN generally accepting input as a 2D image, the intensity projections can combine information across various slices into a single slice that can be provided as input to a CNN. As IPMN and pancreatic cysts are hypo-intensity regions in T1 scans, minimum intensity projection can be used for T1 MRI, whereas maximum intensity projection can be used for T2 MRI because IPMN and pancreatic cysts correspond to hyper-intensity regions in T2 scans. The intensity projections corresponding to T1 and T2 scans can be represented as:

$$I' = \min_{Z_1}[\mathcal{J}(X_1, Y_1, Z_1)] \quad (1)$$

$$J = \max_{Z_2}[\mathcal{J}(X_2, Y_2, Z_2)],$$

where Z1 and Z2 include k slices around $I_u$ and $J_v$, respectively.

At 414, process 400 can provide the minimum intensity projection (e.g., I') to a CNN trained as a general purpose image classifier (e.g., CNN-F trained on the ImageNet data set), and can separately provide the maximum intensity projection (e.g., J') to the CNN (or another instance of the CNN). As described in more detail below in connection with FIG. 5, the CNN-F can include 5 convolutional layers followed by 3 fully-connected layers, and can be configured to accept a 2D image of 224×224 pixels. Accordingly, the minimum intensity projection and maximum intensity projection can be resized and/or cropped to provide an input image of 224×224. The first convolutional layer of CNN-F includes 64 filters and uses a stride length of 4, whereas the other convolutional layers include 256 filters and use a stride length of 1.

At 416, process 400 can receive from the CNN a first set of features Φ for each minimum intensity projection, and a second set of features Ψ for each maximum intensity projection. In some embodiments, the features can be extracted from any suitable layer of the CNN. For example, rather than taking the features from the output (i.e., softmax) layer of the CNN which represent the prediction of which class the input image belongs to, features can be extracted from the second fully connected layer. For example, the features can be the output vector of the second fully connected layer without applying nonlinearities such as ReLU (Rectified Linear Units). In some embodiments, the features extracted from the second fully connected layer (or whichever layer the features are extracted from) can be $l_2$ normalized to obtain the final set of features (e.g., Φ and Ψ).

At 422 (shown in FIG. 4B), process 400 can combine the information from the minimum intensity projection and the maximum intensity projection by calculating a correlation between the minimum intensity projection and the maximum intensity projection for each subject by performing a CCA using the first set of features (e.g., Φ) as a first input matrix, and the second set of features (e.g., Ψ) as a second input matrix.

For example, if $\Phi \in \mathbb{R}^{n \times p}$ and $\Psi \in \mathbb{R}^{n \times q}$ are used to represent the features from the intensity projections of n training images from T1 and T2 scans respectively, each sample can be associated with a corresponding binary label that can be represented as $\mathcal{Y} = [y_1, y_2, \ldots, y_n]$, where $\mathcal{Y} \in \{0,1\}^{n \times 1}$. Within set covariance matrices of $\Phi$ and $\Psi$ can be represented as $C_{\Phi\Phi} \in \mathbb{R}^{p \times p}$ and $C_{\Psi\Psi} \in \mathbb{R}^{q \times q}$, respectively. Additionally, a between set covariance matrix can be represented as $C_{\Phi\Psi} \in \mathbb{R}^{p \times q}$ such that $C_{\Psi\Phi} = C_{\Phi\Psi}^T$. Using these representations, the covariance matrix C can be represented as:

$$C = \begin{pmatrix} \text{cov}(\Phi) & \text{cov}(\Phi, \Psi) \\ \text{cov}(\Psi, \Phi) & \text{cov}(\Psi) \end{pmatrix} = \begin{pmatrix} C_{\Phi\Phi} & C_{\Phi\Psi} \\ C_{\Psi\Phi} & C_{\Psi\Psi} \end{pmatrix}, \quad (2)$$

In some embodiments, CCA can be used to find linear combinations, $\Phi^* = W_\Phi^T \Phi$ and $\Psi^* = W_\Psi^T \Psi$ such that the pairwise correlation between the two sets is maximized. The pairwise correlation between the two sets can be represented as:

$$\text{corr}(\Theta^*, \Psi^*) = \frac{\text{cov}(\Phi^*, \Psi^*)}{\sqrt{\text{var}(\Phi^*) \cdot \text{var}(\Psi^*)}}, \quad (3)$$

where $\text{cov}(\Phi^*, \Psi^*) = W_\Phi^T C_{\Phi\Psi} W_\Psi$, $\text{var}(\Phi^*) = W_\Phi^T C_{\Phi\Phi} W_\Phi$, and $\text{var}(\Psi^*) = W_\Psi^T C_{\Psi\Psi} W_\Psi$. The covariances can then be used to find the transformation matrices, $W_\Phi$ and $W_\Psi$, using the following relationships:

$$C_{\Phi\Phi}^{-1} C_{\Phi\Psi} C_{\Psi\Psi}^{-1} C_{\Psi\Phi} \tilde{W}_\Phi = \Lambda^2 \tilde{W}_\Phi,$$

$$C_{\Psi\Psi}^{-1} C_{\Psi\Phi} C_{\Phi\Phi}^{-1} C_{\Phi\Psi} \tilde{W}_\Psi = \Lambda^2 \tilde{W}_\Psi, \quad (4)$$

where $\tilde{W}_\Phi$ and $\tilde{W}_\Psi$ are the eigenvectors and $\Lambda^2$ is the eigenvalue diagonal matrix.

At 424, process 400 can generate a labeled feature matrix F for each pair of labeled T1 and T2 MRI data based on the results of the CCA. For example, in some embodiments, the final feature matrix can be represented as the sum of the transformed feature matrices from the two modalities as:

$$F = W_\Phi^T \Phi + W_\Psi^T \Psi = \begin{pmatrix} W_\Theta \\ W_\Psi \end{pmatrix}^T \begin{pmatrix} \Phi \\ \Psi \end{pmatrix}, \quad (5)$$

At 426, process 400 can train a classification model (e.g., an SVM) using the labeled feature matrices F as examples of a normal class and examples of an IPMN class. In some embodiments, process 400 can use any suitable technique or combination of techniques to train the SVM to classify unlabeled feature matrices as corresponding to normal pancreas or pancreas having IPMNs. Additionally or alternatively, in some embodiments, the SVM can be trained to distinguish between grades of IPMN (e.g., by labeling IPMN examples as high or low grade).

At 428, process 400 can receive unlabeled T1 and T2 MRI data corresponding to a subject for whom a diagnosis is to be made. In some embodiments, the unlabeled T1 and T2 MRI data can be received using any suitable technique or combination of techniques, such as techniques described above in connection with 402 of FIG. 4A.

At 430, process 400 can preprocess the received unlabeled MRI data (e.g., to normalize and smooth portions of the images) using any suitable technique or combination of techniques, such as techniques described above in connection with 404 of FIG. 4A.

At 432, process 400 can receive a selection of a slice from the unlabeled T1 MRI data that includes the pancreas. In some embodiments, the slice can be selected by a user (e.g., a physician) through a user interface that presents portions of the MRI data.

At 434, process 400 can generate a minimum intensity projection for the selected slice of T1 MRI data, for example, using techniques described above in connection with 406 of FIG. 4A.

At 436, process 400 can receive a selection of a slice from the unlabeled T2 MRI data that includes the pancreas. In some embodiments, the slice can be selected by a user (e.g., a physician) through a user interface that presents portions of the MRI data. Additionally, in some embodiments, multiple slices can be selected at 432 and/or 436, and an analysis can be performed on each slice (e.g., by generating maximum and minimum intensity projections for each slice, and classifying the projections for each slice) to determine whether results are consistent for the various slices.

At 442, shown in FIG. 4C, process 400 can generate a maximum intensity projection for the selected slice of T2 MRI data, for example, using techniques described above in connection with 412 of FIG. 4A.

At 444, process 400 can provide each intensity projection to the CNN for feature extraction (e.g., as described above in connection with 414 of FIG. 4A).

At 446, process 400 can receive, from the CNN, a first set of unlabeled features $\Phi^U$ for each minimum intensity projection, and a second set of unlabeled features $\Psi^U$ for each maximum intensity projection.

At 448, process 400 can calculate a correlation between the unlabeled minimum intensity projection and the unlabeled maximum intensity projection based on a CCA using $\Phi^U$ and $\Psi^U$ as inputs to the CCA. In some embodiments, process 400 can use any suitable technique or combination of techniques to calculate the correlation between the unlabeled minimum intensity projection and the unlabeled maximum intensity projection, such as techniques described above in connection with 422 of FIG. 4B.

At 450, process 400 can generate an unlabeled feature matrix $F^U$ to represent the pair of unlabeled T1 and T2 MRI data based on the correlation(s) calculated at 448 using any suitable technique or combination of techniques (e.g., techniques described above in connection with 424 of FIG. 4B).

At 452, process 400 can provide the unlabeled feature matrix as an input to the trained classification model (e.g., the SVM trained at 426).

At 454, process 400 can receive an indication from the trained classification model of whether IPMNs are likely present in the T1 and T2 MRI data based on the output of the trained classification model (e.g., the output of the trained SVM).

At 456, process 400 can present one or more slices of T1 and/or T2 MRI data to a healthcare provider(s) (e.g., a radiologist, an oncologist, etc.) with information indicative of the likelihood that IPMNs are present. Additionally or alternatively, process 400 can present the minimum projection and/or maximum projection generated at 434 and/or 438 to a healthcare provider with information indicative of the likelihood that IPMNs are present. In some embodiments, the healthcare provider(s) can use the information indicative of the likelihood that IPMNs are present and/or the presented image(s) to discuss a diagnosis with a patient, to determine whether a biopsy (e.g., a fine-needle aspiration (FNA) biopsy) or more detailed scan (e.g., an esophageal ultrasound (EUS)) should be performed to confirm the diagnosis and/or resolve an ambiguous result (e.g., a classification near the threshold between normal and IPMN, combined with a visual inspection indicating that IPMNs may be present).

Figures 5A, 5B:
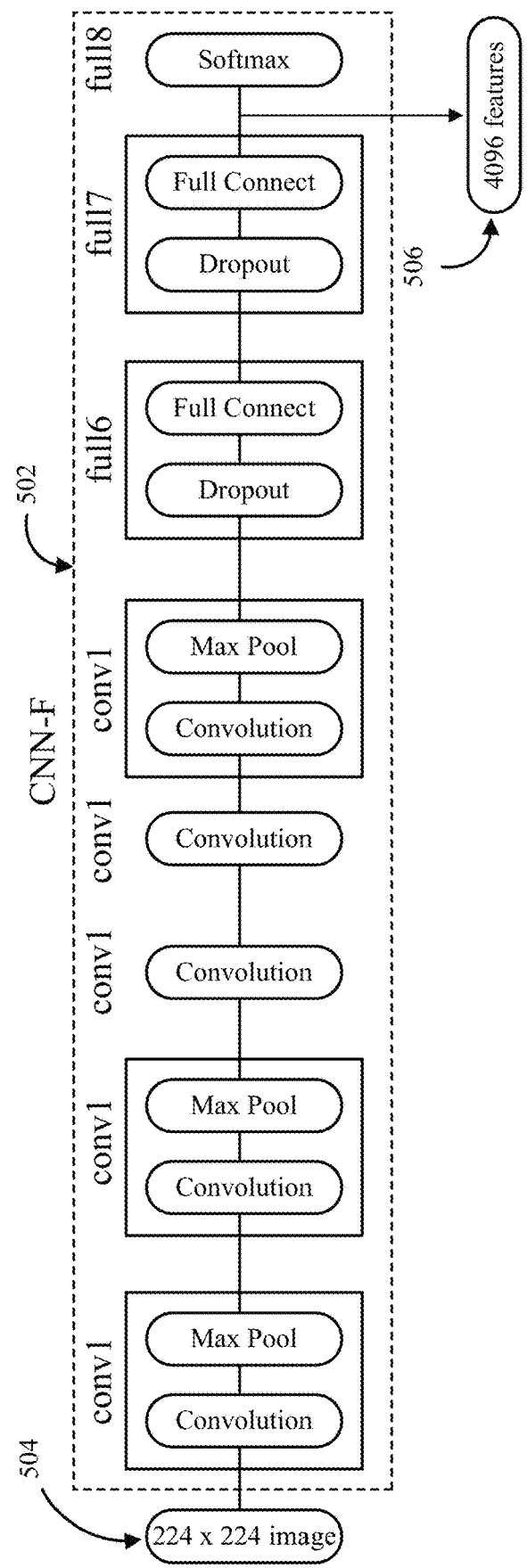
FIG. 5A shows an example of a table specifying parameters of a convolutional neural network that can be trained as a general purpose image classifier that can be used to implement a portion of the mechanisms described herein in accordance with some embodiments.
FIG. 5B shows an example of a topology of a convolutional neural network that has been pre-trained as a general purpose image classifier which can be used to generate features from magnetic resonance imaging data in accordance with some embodiments of the disclosed subject matter.

FIG. 5A shows an example of a table specifying parameters of a convolutional neural network that can be trained as a general purpose image classifier that can be used to implement a portion of the mechanisms described herein in accordance with some embodiments. Note that the table is from Chatfield et al. "Return of the Devil in the Details: Delving Deep into Convolutional Nets," available at arxiv (dot)org, 2014, and describes a particular architecture for a CNN (CNN-F) that can be trained as a general purpose image classifier.

FIG. 5B shows an example 500 of a topology of a CNN 502 that has been pre-trained as a general purpose image classifier which can be used to generate features from MRI data in accordance with some embodiments of the disclosed subject matter. In some embodiments, CNN 502 can have a similar topology to a CNN (CNN-F) described in Chatfield et al. "Return of the Devil in the Details: Delving Deep into Convolutional Nets," available at arxiv(dot)org, 2014. As shown in FIG. 5B, an input image 504 with a resolution of 224×224 pixels can be provided to a first convolutional layer of CNN 502. For example, as described above in connection with 414 of FIG. 4A, a minimum (or maximum) intensity projection can be resized to 224×224 pixels (if necessary) and provided as input to CNN 502. Additionally, in some embodiments, features 506 can be extracted from the second fully connected layer (e.g., the 7th layer). For example, features 506 can include 4,096 values that CNN 502 generates in the second fully connected layer for use by the softmax layer to classify the image.

Figures 6, 7:
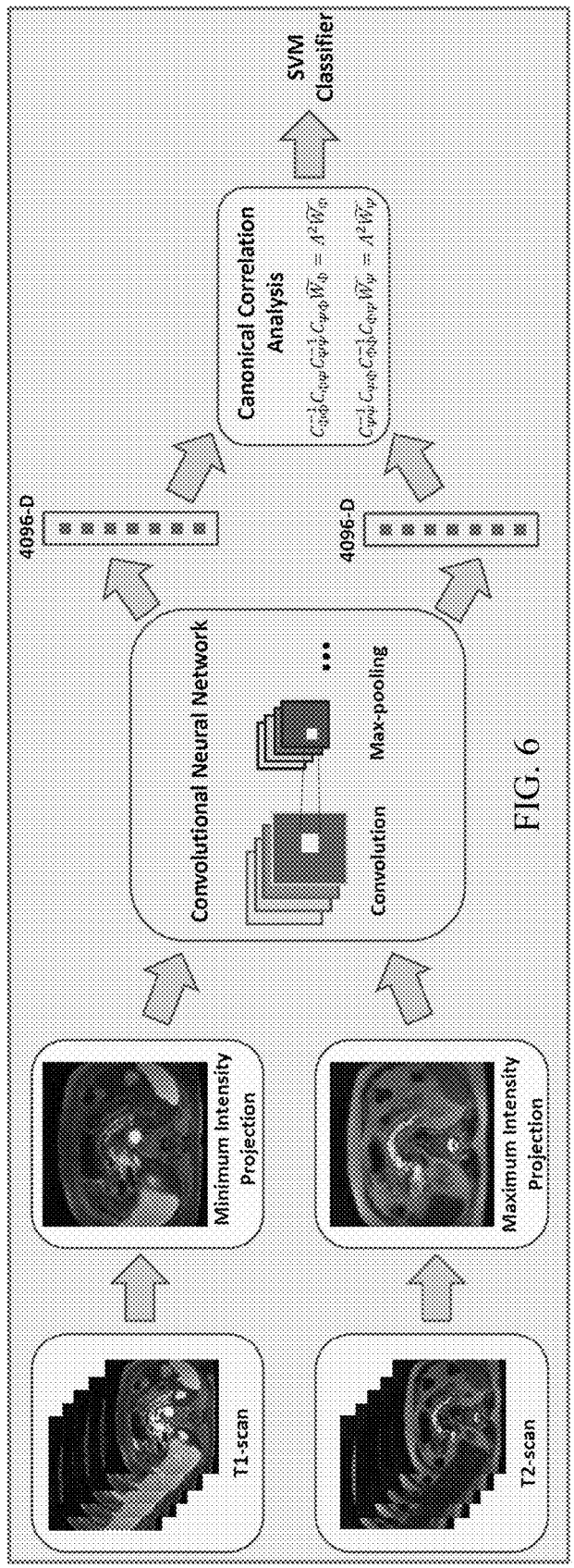
FIG. 6 shows a high level example of process for training a support vector machine to automatically diagnose intraductal papillary mucinous neoplasms using features generated from multi-modal magnetic resonance imaging data in accordance with some embodiments of the disclosed subject matter.
FIG. 7 shows an example of a table of results comparing the accuracy, sensitivity, and specificity of a system for automatically diagnosing intraductal papillary mucinous neoplasms using multi-modal magnetic resonance imaging data implemented in accordance with some embodiments of the disclosed subject matter.

FIG. 6 shows a high level example of process for training a support vector machine to automatically diagnose IPMN using features generated from multi-modal MRI data in accordance with some embodiments of the disclosed subject matter.

FIG. 7 shows an example of a table of results comparing the accuracy, sensitivity, and specificity of a system for automatically diagnosing IPMN using multi-modal MRI data implemented in accordance with some embodiments of the disclosed subject matter. As shown in FIG. 7, a system for automatically diagnosing IPMNs using multi-modal MRI data that was implemented in accordance with some embodiments of the mechanisms described herein achieved higher accuracy and higher specificity than using the T1, T2, or concatenated T1 and T2 MRI data.

Figure 8:
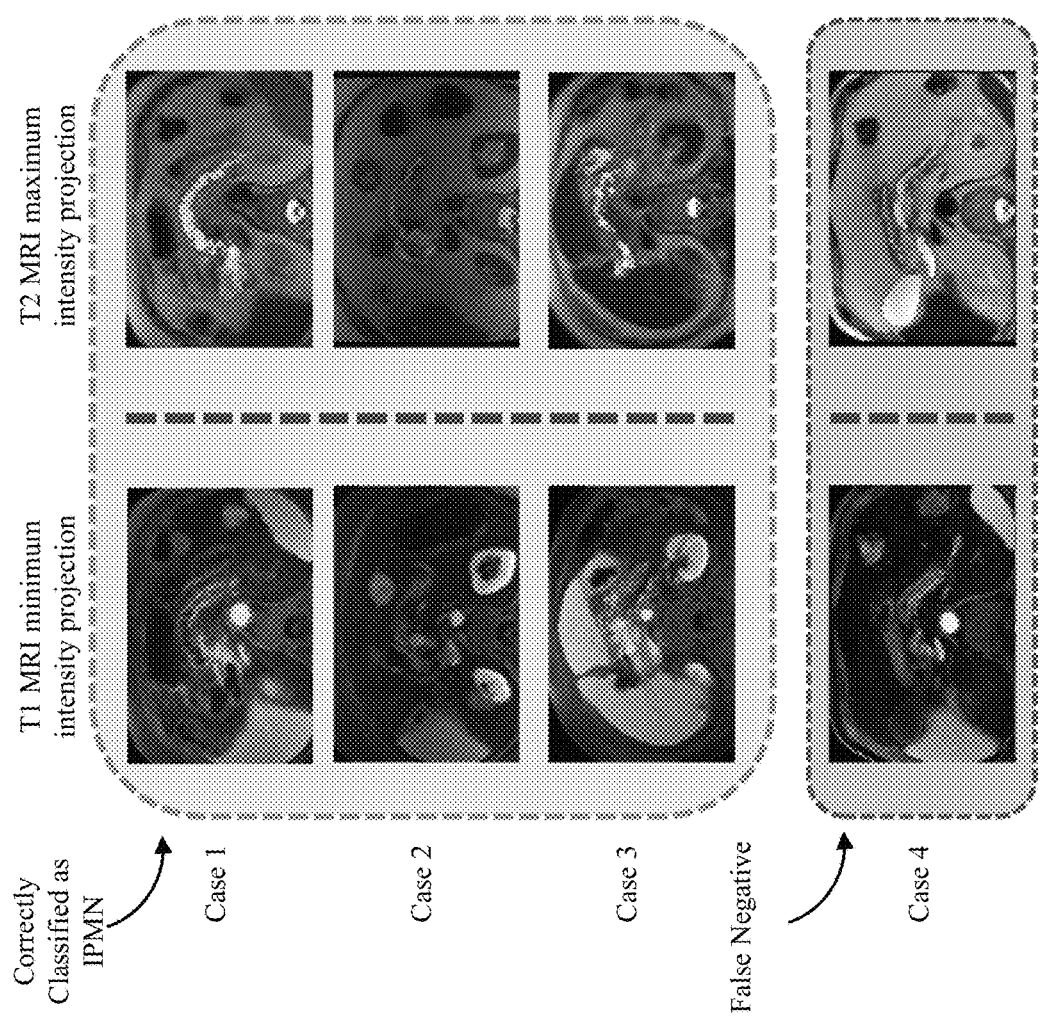
FIG. 8 shows examples of pairs of T1 minimum intensity projections and T2 maximum intensity projections that were evaluated using a system for automatically diagnosing intraductal papillary mucinous neoplasms using multi-modal magnetic resonance imaging data implemented in accordance with some embodiments of the disclosed subject matter.

FIG. 8 shows examples of pairs of T1 minimum intensity projections and T2 maximum intensity projections that were evaluated using a system for automatically diagnosing IPMN using multi-modal MRI data implemented in accordance with some embodiments of the disclosed subject matter.

FIG. 9 shows an example of a table showing demographics of subject's depicted in multi-modal MRI data used to train and evaluate a system for automatically diagnosing IPMN using multi-modal MRI data implemented in accordance with some embodiments of the disclosed subject matter.

FIG. 10 shows an example of a table showing manually determined features present in the multi-modal MRI data used to train and evaluate a system for automatically diagnosing IPMN using multi-modal MRI data implemented in accordance with some embodiments of the disclosed subject matter, and performance of the system.

FIG. 11 shows an example of a table showing a comparison of the performance of conventional techniques and a system for automatically diagnosing IPMN using multi-modal MRI data implemented in accordance with some embodiments of the disclosed subject matter.

Four previous studies have compared the diagnostic accuracy of the AGA and Fukuoka guidelines. All studies concluded that Fukuoka achieves a higher sensitivity for high risk lesions (i.e., high-risk dysplasia and adenocarcinoma). Two of the studies concluded that the Fukuoka guidelines achieve higher specificity, and the other two concluded that the AGA guidelines achieve higher specificity. To provide a consistent basis for comparison, the Fukuoka guidelines and AGA guidelines were used to evaluate the same MRI data used to train a system for automatically diagnosing IPMN using multi-modal MRI data implemented in accordance with some embodiments of the disclosed subject matter. As shown in FIG. 11, in agreement with the previous studies, Fukuoka was more sensitive and AGA was more specific. Other guidelines (e.g., Sendai and ACR) are less frequently used and were not used as points of comparison with the system for automatically diagnosing IPMN using multi-modal MRI data implemented in accordance with some embodiments of the disclosed subject matter. Areas under the curve for the Fukuoka and AGA guidelines were similar to those previously reported. With the exception of the higher specificity achieved by the AGA guidelines, the system for automatically diagnosing IPMN using multi-modal MRI data implemented in accordance with some embodiments of the disclosed subject matter achieved diagnostic accuracy comparable, and potentially superior, to the conventional techniques.

When screening pre-cancerous lesions, such as IPMNs, sensitivity is often preferred over specificity. For example, currently available automated diagnosis is typically used as a screening tool that has to be verified by radiologists and complementary studies. In such an example, a false positive result will lead to additional testing such as EUS and/or FNA, prior to determining a particular treatment (e.g., pancreatectomy). By contrast, a false negative can result in the window of time during which treatments (e.g., a surgical intervention for adenocarcinoma resection) that may be efficacious closing. As shown in FIG. 11, the mechanisms described herein achieved higher sensitivity than AGA and the Fukuoka guidelines.

A system for automatically diagnosing IPMN using multi-modal MRI data implemented in accordance with some embodiments of the disclosed subject matter was evaluated on a dataset including post-contrast T1 and T2 MRI axial scans from 139 subjects. The scans were labeled by a radiologist as normal or IPMN. Out of 139 scans, 109 were from subjects diagnosed with IPMN, and the remaining 30 were from subjects diagnosed as normal. The in-plane spacing (i.e., the distance between pixels in the x and y directions within the xy-plane) of the T1 scan ranged from 0.664 mm to 1.484 mm and that of T2 scan from 0.468 mm to 1.406 mm.

To account for misalignments, multi-resolution image registration was performed using image pyramids. The registration results were examined and images with misregistration were removed from the final evaluation set. The final evaluation set included 139 scans from each modality a 10 fold cross validation was performed over the dataset. The minimum (and maximum) intensity projection images from T1 (and T2) scans were fed into the deep CNN-F network and feature representation from each of these images was used to obtain the final CCA based discriminative representation (e.g., as described above in connection with FIGS.

3-6). A SVM was trained and used to obtain the final classification labels (i.e., normal or IPMN).

As shown in FIG. 7, a system implemented in accordance with some embodiments of the mechanisms described herein was compared to single modality and feature concatenation based approaches. Since there exists an imbalance between the number of positive and negative examples, Adaptive Synthetic Sampling (ADASYN) was used to generate synthetic samples, which enabled generation of synthetic feature examples of the minority class (i.e., normal).

FIG. 7 shows results achieved by a system implemented in accordance with some embodiments of the mechanisms described herein and results using other techniques. As shown in FIG. 7, accuracy of the mechanisms described herein significantly outperformed the single modality and feature concatenation based approaches. The T1 based classification yielded the highest sensitivity but with very low specificity. For IPMN classification, low specificity can be a serious problem as that can lead to unwarranted biopsy, surgery, and resection. In this regard, a system implemented in accordance with some embodiments of the mechanisms described herein achieved more than a 30% improvement in specificity in comparison with the feature concatenation based approach. Note that since the mechanisms described herein are based on the correlation and covariance in the data, it does not require explicit sample balancing using ADASYN. Additional tests were performed using features from various layers of CNN-F (e.g., other than the second fully connected layer), and from deeper residual networks such as ResNet-50, ResNet-101, and ResNet-152. The best classification results, were obtained using the second fully-connected layer of CNN-F.

In some embodiments, the mechanisms described herein can provide information for radiologists attempting to diagnose invasive pancreatic carcinoma. In contrast to previous studies, the mechanisms described herein can use deep CNN feature representations for IPMN diagnosis. Additionally, the mechanisms described herein can use feature level fusion of two different MRI imaging modalities (i.e., T1 and T2 scans) to achieve generally better results than are achieved using either modality alone.

Additionally, the mechanisms described herein do not require segmentation (manual or automatic) of the pancreas or cysts, which is required by some other techniques. Rather, in some embodiments, the mechanisms described herein can perform an automatic diagnosis based on a single slice where pancreatic tissues can be prominently observed. Additionally, using the intensity projections across consecutive set of slices can mitigate problems that may arise because of sub-optimal slice selection.

A retrospective review of cases that have undergone pancreatectomy and have confirmed IPMN was performed. Patients that had an MRI prior to surgery were included. A priori, limits were placed to include similar number of cases with low grade dysplasia, high grade dysplasia, and invasive adenocarcinoma. Additionally a sample of MRIs done for non-pancreatic indications (e.g., cirrhosis screening for hepatocellular carcinoma) were reviewed, and images were included if no cystic lesions were reported.

Demographic, clinical (e.g., presenting symptoms and history of pancreatic disease), and histopathology variables (e.g. type of invasive carcinoma) were recorded. Results of any EUS and/or FNA that was performed were recorded as well.

MRI studies were reviewed and interpreted by a radiologist after the regular protocol. Based on images and radiology reports, studies were classified according to the AGA guidelines (presence of 0 to 3 high risk features), and the Fukuoka guidelines (main duct IPMN, presence of high risk features or worrisome features) by two un-blinded investigators. If multiple cystic lesions were identified in the pancreas, all were recorded for descriptive analysis. Only the largest lesion was classified by AGA, Fukuoka and the mechanisms described herein.

Images underwent an N4 bias field correction to normalize variations in image intensity. A minimum and maximum intensity projections were computed corresponding to T1 and T2 scans respectively. These two projections were then fed into a pre-trained CNN to obtain feature representation. After feature extraction, a 4096-D vector was created for every image. These vectors were sent for CCA, which combined information from T1 and T2 to obtain discriminative and transformed feature representation. Finally an SVM classifier was used to assign one of the three final labels: normal pancreas, low-grade IPMN or high-grade IPMN/adenocarcinoma.

Sensitivity and specificity were calculated based on pathology results. Response operator curves (ROC) graphs were elaborated and areas under the curve were estimated. Areas under the ROC were compared using tests of equality of ROC areas. Analysis was done using Stata/SE 13.0 software (available from StataCorp LLC, College Station, Tex.). Study protocol was approved by Mayo Clinic IRB.

171 abdominal MRIs were identified on initial review: 39 MRIs done for non-pancreatic indications showed no pancreatic cysts and 132 MRIs had IPMN followed by pancreatectomy confirming histological IPMN. 32 cases were excluded due to history of previous pancreas surgery, overlapping diagnosis, poor image quality or missing pathology report. 139 cases were included for final analysis.

Most patients were female (58.3%); mean age was 65.3±11.9 years; 89.2% were White; average BMI was 26.5±4.8 Kg/m2 and 59.0% were smokers. Indications for abdominal imaging were diverse, but 43.8% presented with abdominal pain, 5.8% had steatorrhea and 23.7% weight loss. 21.6% patients had an episode of acute pancreatitis and 9.4% had findings suggestive of chronic pancreatitis. 17 patients (12.2%) had a family history of pancreatic cancer.

Of those who had pancreatectomy, 48 (34.5%) had IPMN with low-grade dysplasia, 20 (14.4%) IPMN with high-grade dysplasia, and 40 (28.8%) adenocarcinoma in the background of IPMN.

One quarter to one third of patients had two or more IPMNs lesions in the pancreas. Most common anatomic location was the pancreatic head. Some lesions, in particular adenocarcinoma, showed areas of enhancement.

97 (69.8%) patients received an EUS after MRI. Of those, 29 (29.9%) showed separated cysts and 77 (79.4%) had fine needle aspiration (FNA). Of all FNA samples 24.7% were non diagnostic, 48.0% had mucinous epithelium, 10.4% atypical epithelial cells, and 16.9% confirmed adenocarcinoma.

Sensitivity and specificity of a system for automatically diagnosing IPMN using multi-modal MRI data implemented in accordance with some embodiments of the disclosed subject matter to detect dysplasia (low or high grade) was 89.6% and 51.6%, respectively. Sensitivity and specificity to identify high-grade dysplasia or cancer was 75.0% and 78.5%, respectively.

Figure 12:
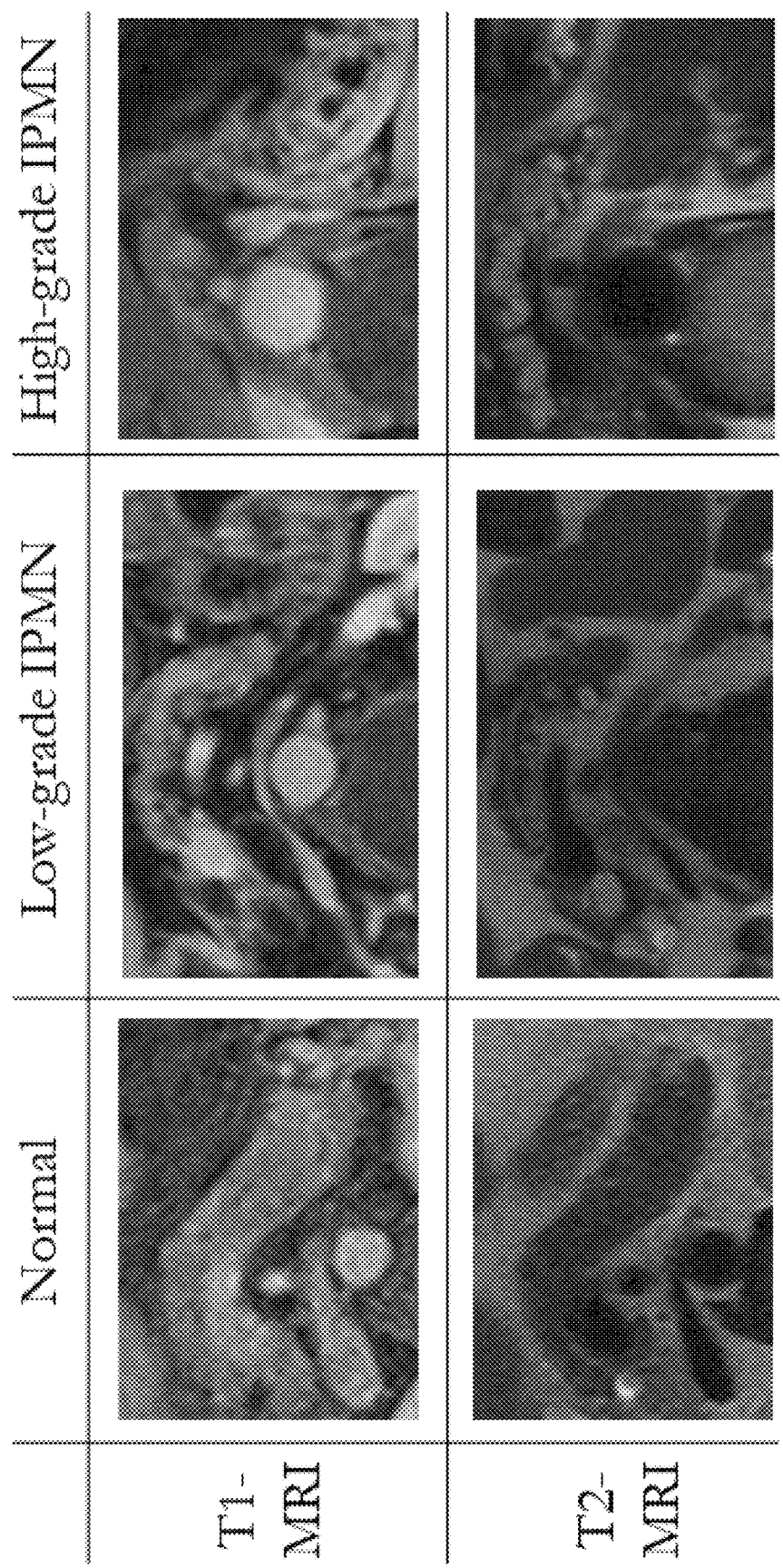
FIG. 12 shows examples of T1 and T2 MRI images of a subject's normal pancreas, examples of T1 and T2 MRI images of a subject's pancreas that includes low-grade IPMNs, and examples of T1 and T2 MRI images of a subject's pancreas that includes high-grade IPMNs.

FIG. 12 shows examples of T1 and T2 MRI images of a subject's normal pancreas, examples of T1 and T2 MRI images of a subject's pancreas that includes low-grade IPMNs, and examples of T1 and T2 MRI images of a subject's pancreas that includes high-grade IPMNs. IPMNs are a radiographically detectable neoplasm that is found in the main and branch pancreatic ducts and is often a precursor to pancreatic ductal adenocarcinoma. IPMNs have the potential to progress into invasive carcinoma, as a large proportion of main duct-IPMNs exhibit malignant progression. FIG. 12 shows example MRI images with the associated grade of IPMN, where the images are cropped to a regions of interest (ROI) surrounding the pancreas. The IPMNs present in the images were graded in a pathology report after surgery as being normal, low-grade IPMN, high-grade IPMN, or invasive carcinoma. In general, early accurate detection of potentially malignant IPMNs may help diagnose pancreatic cancer sooner and, in turn, increase the very low 5-year survival rates. While progress has been made in diagnosing and managing IPMNs pre-operatively using radiographic criteria and international consensus guidelines, mechanisms described herein can provide additional data that can be used to distinguish IPMNs in the pancreas and differentiate between grades potentially more efficiently and effectively than current standards.

In general, while newer and more powerful deep network architectures continue to emerge, these architectures have a particular structure and often take weeks to train as general image classification models (e.g., based on ImageNet data). Accordingly, any changes to the architecture (e.g., to adapt the architecture to 3D data from 2D data) would typically require retraining the entire model. This can be difficult due to a lack of suitable training data (e.g., labeled 2D images are much more available than labeled 3D images). This can be especially problematic in the medical imaging domain where annotated data is often extremely limited and utilizing pre-trained deep networks often leads to dramatic performance increases versus training a network using only medical imaging data. Additionally, due to the 3D nature of most medical imaging modalities, 3D networks tend to outperform their 2D counterparts, but most pre-trained networks exist only in 2D versions. One approach can be to attempt to train a novel architecture and/or a variant of a pre-trained architecture from scratch. However, this generally impractical and/or prohibitively expensive for many applications, especially where there is a lack of training data and/or a specialized application. For example, while conventional training techniques on large datasets (e.g., using the ImageNet dataset) can be a multi-week process, and/or require large clusters of expensive GPUs for processing.

In some embodiments, the mechanisms described herein can use network inflation techniques to convert 2D convolutional kernels and pooling operations to a 3D counterpart, and can replicate the kernels along the third dimension. Additionally, in some embodiments, the value of the weights can be dividing by the number of replications to preserve relatively similar activation values. For example, the mechanisms described herein can inflate relatively deep, advanced, and complicatedly-connected networks. As another example, the mechanisms described herein can be used to transfer weights when multiple imaging modalities are used (e.g., T1 and T2 MRI).

In some embodiments, the mechanisms described herein can use various fusion strategies (e.g., early fusion, intermediate fusion, or late fusion) to combine information from different imaging modalities. For example, mechanisms described herein can use one or more early (e.g., pixel-level) fusion techniques. In a more particular example, images from different modalities can be concatenated at the pixel level before being input to the network. As another example, mechanisms described herein can use one or more late fusion techniques. In a more particular example, inputs can be fed to a neural network separately and the final embeddings can be concatenated and fed to final classification layers (e.g., one or more fully connected layers). As yet another example, mechanisms described herein can use one or more intermediate fusion techniques. In a more particular example, information from multiple modalities can be combined somewhere in a neural network, for example after a particular concatenation or pooling layer (e.g., an equivalent layer in different parts of a network, within layers that output data having the same or a similar resolution, etc.). In some embodiments, the type of fusion that is used can be based on how similar the information is in each modality. For example, when the different modalities are relatively similar early fusion or intermediate fusion may produce superior results. As another example, when the different modalities are relatively different, later fusion may product superior results.

In some embodiments, using information from multiple modalities as input to a neural network can add an additional challenge for transferring weights from pre-trained networks, which typically accept only three-channel images (e.g., RGB images) as input. In such embodiments, transferring the weights of the earlier layers in a neural network can be especially important to support transfer learning, as the lowest-level layers can generate useful features across for many different types of images, while higher-level layers can become more specialized to the specific training data.

In some embodiments, the mechanisms described herein can be used to generate inflated pre-trained neural networks that can be trained (e.g., using transfer learning techniques) to classify images from a relatively small training dataset (e.g., on the order of dozens to hundreds of labeled examples). For example, the mechanisms described herein can be used to generate an inflated version of an Inception-based convolution neural network (e.g., based on Inception V3 described in Szegedy et al., "Rethinking inception architecture for computer vision," Proceedings of the IEEE conference on computer vision and pattern recognition, pp. 2818-2826 (2016), which is hereby incorporated by reference herein in its entirety) that has been pre-trained (e.g., based on ImageNet images) as a general image classification CNN. As another example, the mechanisms described herein can be used to generate an inflated version of a DenseNet-based convolution neural network (e.g., based on DenseNet121 described in Huang et al., "Densely connected convolutional neural networks," Proceedings of the IEEE conference on computer vision and pattern recognition, pp. 4700-4708 (2017), which is hereby incorporated by reference herein in its entirety) that has been pre-trained (e.g., based on ImageNet images) as a general image classification CNN.

In some embodiments, mechanisms described herein can generate an inflated CNN by transferring weights from a pre-trained 2D CNN to a new 3D kernel. Additionally, in some embodiments, mechanisms described herein can further inflate a pre-trained CNN by further expanding the pre-trained kernels to apply to any number of input modalities and different fusion techniques. For example, by expanding the kernels to account for different modalities, mechanisms described herein can facilitate image-based diagnosis that is configured to utilize information from multiple image modalities provided as input.

Figure 13:
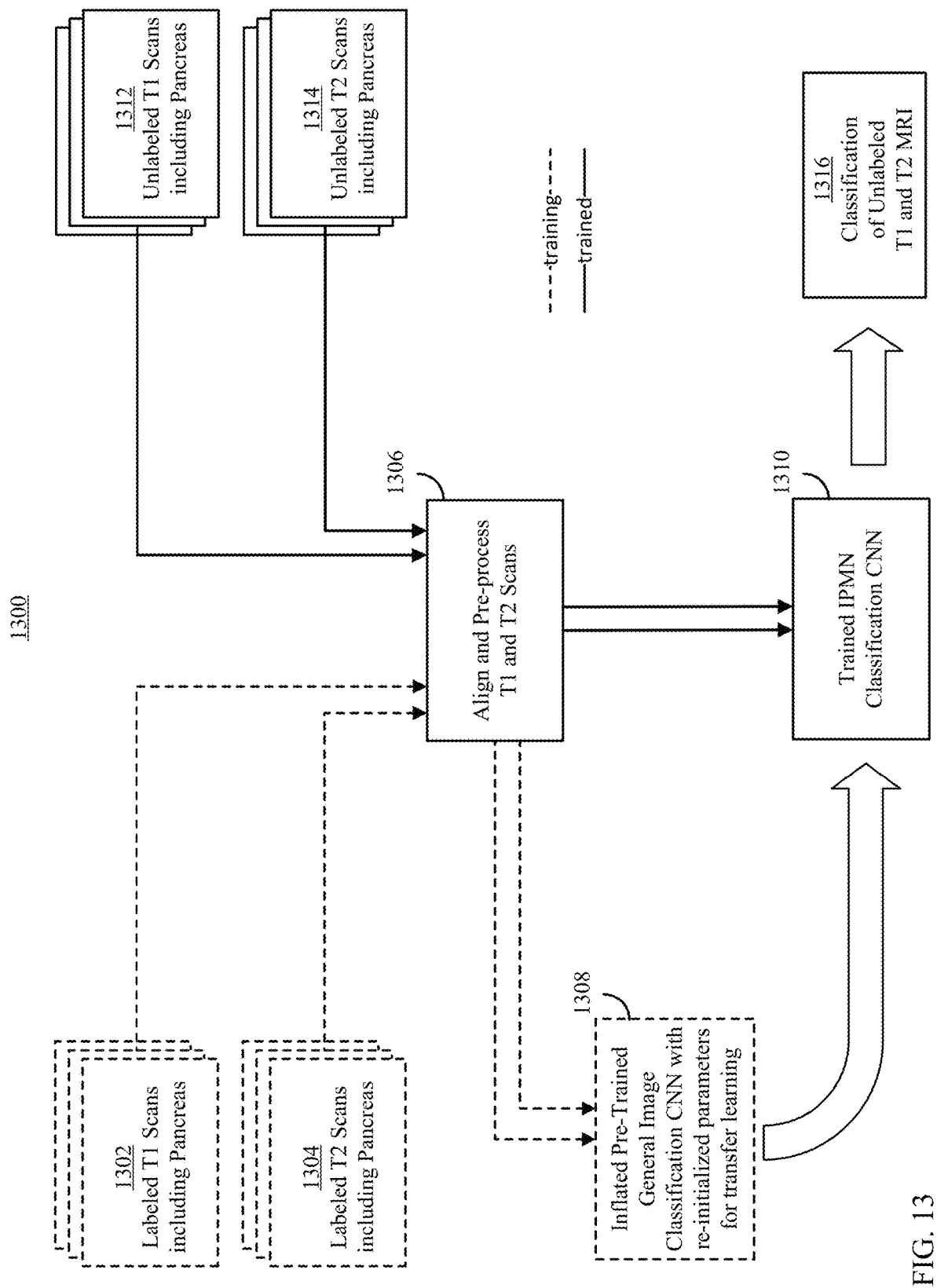
FIG. 13 shows an example of a flow for training and using mechanisms for automatically diagnosing IPMN using multi-modal MRI data in accordance with some embodiments of the disclosed subject matter.

FIG. 13 shows an example 1300 of a flow for training and using mechanisms for automatically diagnosing IPMN using multi-modal MRI data in accordance with some embodiments of the disclosed subject matter. As shown in FIG. 13, labeled examples 1302 of T1 scans of a variety of subjects that include at least one image of the subject's pancreas can be used as training data, with each labeled T1 scan being labeled as corresponding to a "normal" pancreas (or a pancreas lacking IPMNs) or labeled as having IPMNs of a particular severity. For example, a user(s) (e.g., a physician) can select an image from each labeled T1 scan 1302 that shows the subject's pancreas.

Similarly, labeled examples 1304 of T2 scans of the variety of subject's that include at least one image of the subject's pancreas can be used to generate additional training data. For example, a user(s) (e.g., a physician) can select an image from each labeled T2 scan 1304 that shows the subject's pancreas.

In some embodiments, using a single slice as training data may lead to overfitting to the training data, and may miss potentially important contextual information included in the other slices. Accordingly, in some embodiments, additional information can be introduced based on surrounding images (e.g., adjacent slices). For example, a user can select a particular image to be used as training data, and the adjacent k slices (e.g., 2, 4, etc.) on either side of the image can also be used as training data. In some embodiments, a user can select an image from the T1 or T2 scans, and a corresponding scan from the other imaging modality can be automatically selected (e.g., along with the adjacent k slices).

In some embodiments, at 1306 each T1 scan and/or T2 scan (or set of scans) can be aligned and preprocessed. For example, T1 scans and/or T2 scans can be aligned using one or more b-spline registration techniques. As another example, T1 scans and/or T2 scans can be preprocessed using an N4 bias field correction technique. As yet another example, T1 scans and/or T2 scans can be preprocessed by applying a curvature anisotropic image filter. As described below, using an early fusion technique, the k slices of each modality can be concatenated along the channel axis (e.g., the first slice of T1 image data can be input to a first modality channel of a first depth channel of an inflated CNN, and the first slice of T2 image data can be input to a second modality channel of the first depth channel of an inflated CNN) and the concatenated data can be input to the network as a single input image. Alternatively, using a later fusion technique (e.g., an intermediate or later fusion technique), the k slices of each modality can be input to a separate CNN, and the output of a particular layer of each CNN can be concatenated along the channel axis and input to a remainder of the network.

In some embodiments, transfer learning techniques can be used to train an inflated pre-trained general image classification CNN 1308. For example, the weights of the final fully connected layer(s) can be initialized (e.g., to a random value, to a default value), and the initialized weights can be trained using the training data (e.g., labeled T1 scans 1302 and labeled T2 scans 1304).

In some embodiments, inflated pre-trained CNN 1308 can be generated from a 2D network with pre-trained weights that can be used to classify MRI images of a pancreas without substantial modifications to the overall network architecture. For example, all 2D layers of the pre-trained network can be converted to a corresponding 3D counterparts (e.g., a 2D convolution layer can be converted to a 3D convolution layer, a 2D pooling layer can be converted to a 3D pooling layer, etc.). In some embodiments, convolutional kernel size, pooling size, and/or stride length in the added (e.g., third) dimension can be somewhat application dependent. For example, if 30 frame per second data video is to be used for training and classification, relatively larger kernels, strides, and pooling can be used in the added dimension due to the relatively robust amount of information included in video data. As another example, because the pancreas typically only occupies a relatively small number of slices of an abdominal portion of an MRI, strides lengths that are relatively short (e.g., a stride of 1) can be used for the added dimension. In such an example, square kernels (e.g., 2×2 kernels) in the 2D network can be extend to cubes (e.g., a 2×2×2 kernel). Additionally, in such an example, linear kernels (e.g., can be maintained as linear kernels in the new dimension (e.g., a h×1 kernel can be implemented as an h×1×1 kernel, or a 1×w kernel can be implemented as a 1×w×1 kernel).

In some embodiments, weights from the 2D kernels can be transferred to the 3D kernels by bootstrapping them along the third dimension. For example, this can be accomplished by tiling the weights along the new dimension, then dividing all of the weight values of the kernel by the new depth of the kernel. This division can be important to keep the network activations approximately the same from layer to layer. Note that while it may be relatively straightforward to generate these weights when working with RGB images, it can quickly become complicated with non-three-channel images and multiple imaging modalities, as described below.

In some embodiments, after training inflated pre-trained general image classification CNN 1308 is complete, a trained IPMN classification CNN 1310 can be generated and used to classify a pancreas of a subject using unlabeled T1 scans 1312 and unlabeled T2 scans 1314 depicting the subject's pancreas.

In some embodiments, trained IPMN classification CNN 1310 can provide a classification 1316 of the subject of the T1 and T2 scans that is indicative of the predicted presence and/or grade of IPMNs. For example, the subject can be classified as having a "normal" pancreas, or as having IPMNs of various grade present.

Figure 14:
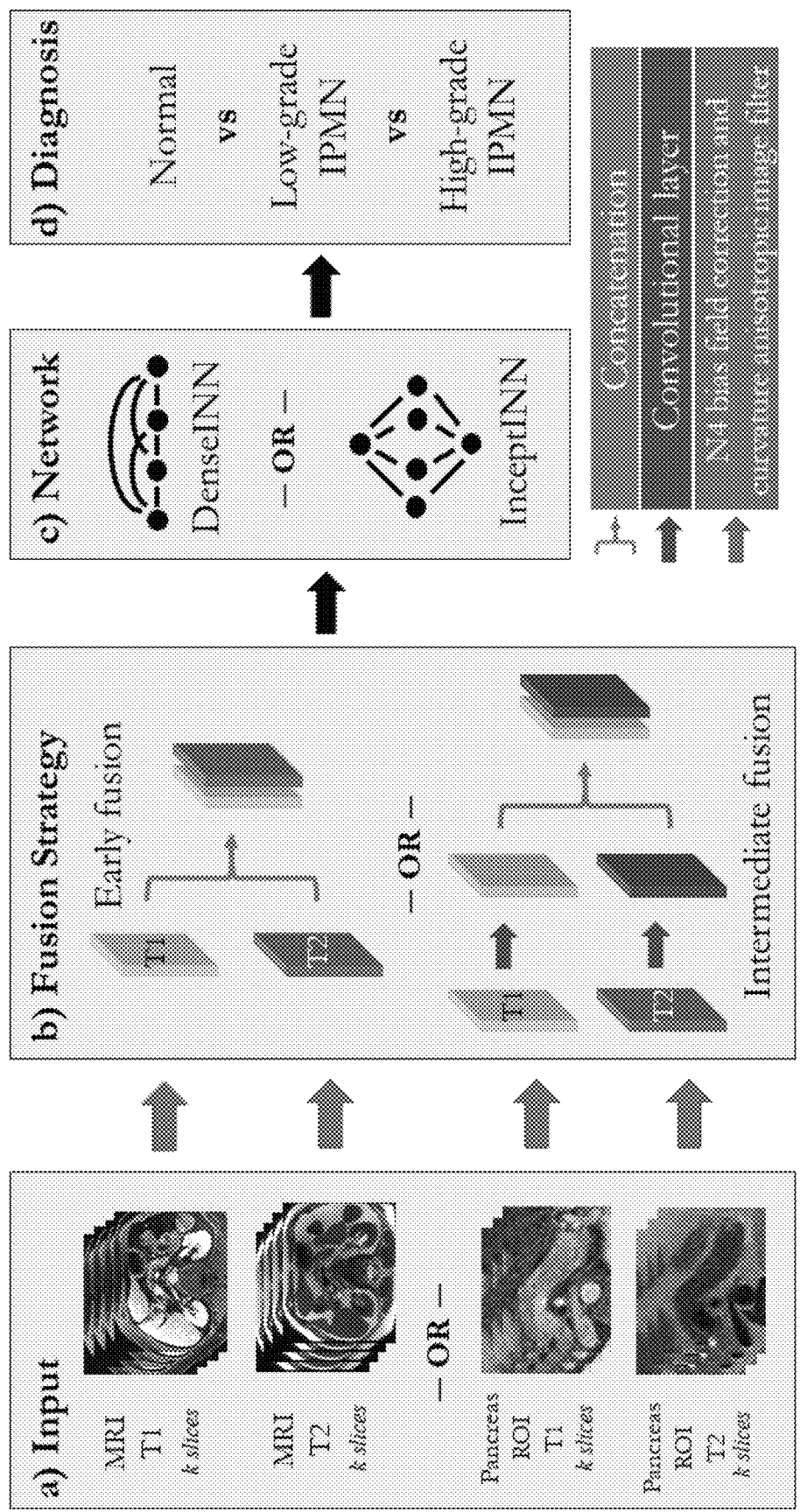
FIG. 14 shows high level examples of processes for using systems for automatically diagnosing IPMN using multi-modal MRI data in accordance with some embodiments of the disclosed subject matter.

FIG. 14 shows high level examples of processes for using systems for automatically diagnosing IPMN using multi-modal MRI data in accordance with some embodiments of the disclosed subject matter. As shown in FIG. 14, during training and testing, k slices from either whole MRI scans or cropped pancreas-ROIs can be used as input to an inflated deep network. Prior to being provided as input to the network, the multimodal MRI scans can be preprocessed by first aligning the T1 scans to the T2 scans using b-spline registration, then performing N4 bias field correction and applying a curvature anisotropic image filter. Following pre-processing, the k slices of each modality can either be concatenated along the channel axis and input to the network or input separately, depending on which type of fusion technique is being used. If intermediate fusion is chosen, each modality can be passed through a separate convolutional layer before being concatenated and passed through the remainder or the network. At the end of the network, a softmax output over three values can be output, representing the probability of our three possible grades of IPMN.

Figure 15:
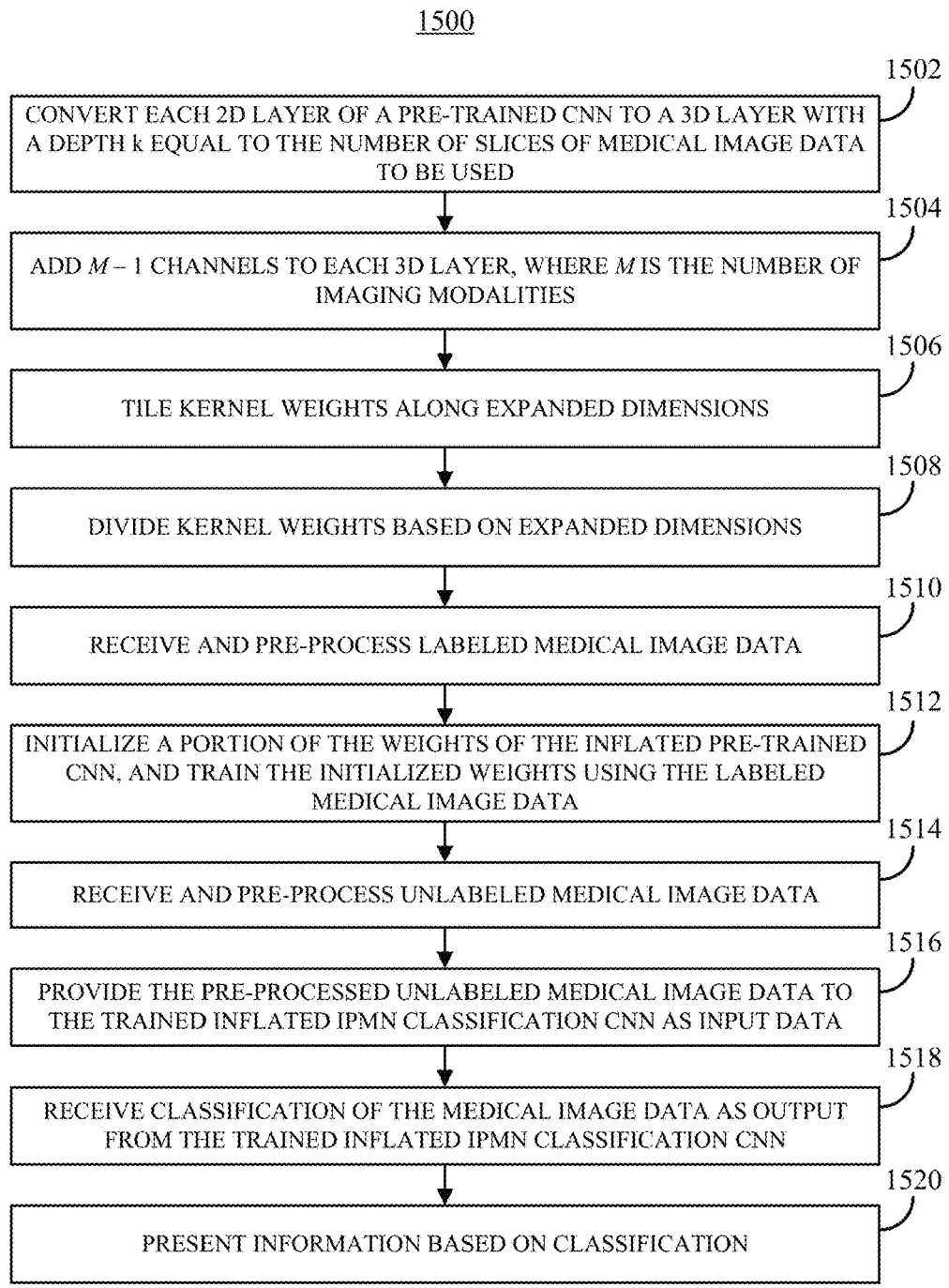
FIG. 15 shows another example of a process for training and using a system for automatically diagnosing IPMN using multi-modal MRI data in accordance with some embodiments of the disclosed subject matter.

FIG. 15 shows another example 1500 of a process for training and using a system for automatically diagnosing IPMN using multi-modal MRI data in accordance with some embodiments of the disclosed subject matter. At 1502, process 1500 can convert each 2D layer of a pre-trained CNN (e.g., a deep convolutional neural network, such as an Inception-based CNN or a DenseNet-based CNN) to a corresponding 3D layer with a depth of k corresponding to the number of slices of MRI data to be used as input to the trained CNN. For example, if the pre-trained CNN is a 2D network with 3 color channels, at 1502 process 1500 can replicate each color channel along the depth axis to result in a 3D network with 3 color channels at each depth.

At 1504, process 1500 can add M−1 channels to the CNN, where M corresponds to the number of imaging modalities to be used. For example, if two imaging modalities are to be used, the entire CNN can be replicated a single time to produce a CNN with two modality channels. For example, if the pre-trained CNN has been expanded to be a 3D network with 3 color channels at each depth, at 1504 process 1500 can replicate each color channel at each depth along the a modality axis to result in a 3D network with 2 modality channels at each depth, and 3 color channels for each modality channel.

In some embodiments, using an intermediate fusion strategy, the first convolutional layer can transfers copies of its weights (which can also tiled along the new third dimension corresponding to the number of slices) to each modalities' individual convolution layer. In such embodiments, initial layer kernels can be divided only by the length of the new third dimension. After these layers, the results can be concatenated and provided as input to the remainder of the network. In some embodiments, one or more layers after concatenation can now be the ones which have M copies made of its kernels along the input channel dimension and its values divided by M.

At 1506, process 1500 can tile the pre-trained kernel weights along each of the expanded dimensions. For example, if the expanded CNN is a 3D network with 2 modality channels at each depth, and 3 color channels for each modality channel, the original 2D kernel weights can be replicated across the depth direction, and along the modality direction within each depth.

At 1508, process 1500 can divide the kernel weights along the expanded dimensions. For example, the kernel weights can be divided by the number of depth dimensions into which the kernel was expanded. In a more particular example, for a 2D network expanded into a 3D network, weights of kernels that are expanded along the depth dimension can be divided by the new depth d (e.g., which can be equal to the number of slices k of medical imaging data to be used as input to the CNN). As another more particular example, for a 2D network expanded into a 3D network with M modality channels, weights of kernels that are expanded along the depth dimension and modality dimension can be divided by the new depth d of the network and by the new number of imaging modality channels M.

At 1510, process 1500 can receive and pre-process labeled medical image data. For example, process 1500 can receive labeled T1 MRI scans and T2 MRI scans depicting the pancreas of various subjects. In some embodiments, process 1500 can use any suitable technique or combination of techniques to pre-process the received labeled medical image data, such as one or more techniques described above in connection with 1306 of FIG. 13. In some embodiments, process 1500 can receive any suitable number of slices corresponding to each subject. For example, if the CNN is to be trained to use five slices, process 1500 can receive five or more slices and can select five slices to use as training data. In such an example, the slices to be used as training data can be automatically selected (e.g., without user input) based on a segmentation of the pancreas. Alternatively, the slices to be used as training data can be semi-automatically selected (e.g., with at least some user input) based on a selection of a slide that includes the largest amount of pancreas and/or any other suitable criterion or criteria.

At 1512, process 1500 can initialize a portion of the weights of the inflated pre-trained CNN, and can train the weights that have been initialized using the labeled medical image data received at 1510. For example, process 1500 can implement one or more transfer learning techniques by resetting the pre-trained weights in a number of the final layers of the inflated pre-trained CNN, such as the weights in the final fully connected layer(s) and the softmax layer. In some embodiments, process 1500 can train the CNN to generate a trained IPMN diagnosis CNN using any suitable stopping criteria. For example, if performance improvement falls below a threshold, process 1500 can end the training process. As another example, after a pre-determined number of training epochs, process 1500 can end the training process.

In some embodiments, because medical imaging modalities (e.g. MRI, computed tomography, ultrasound, etc.) are single-channel (e.g., a brightness channel only), input images can be replicated (e.g., tiled to create three-channel images in which each channel is identical) and provided to each of the color channels of the pre-trained CNN. While this would be sufficient for a single modality input, it is not appropriate for inputting multiple modalities. For example, using an early fusion strategy, three-channel images can be generated for each mode, and the modes can be concatenated prior to input into the network. In light of this input method, in some embodiments, a copy of the first layer's kernels can be created for each modality M in addition to copying the kernels along the newly added dimension (e.g., $kern_h \times kern_w \times kern_d * 1 \times |M| *$ color channels). As another example, using an intermediate fusion strategy, process 1500 can transfer copies of the original first convolutional layer weights (e.g., also tiled along the new third dimension) to each modality's individual convolution layer. Because these layers are not also inflated along the modality dimension, the initial layer kernels can be divided by the length of the added dimension. After these layers, the results can be concatenated and fed into the remainder of the network. The first layer after concatenation can be a layer which has M copies made of its kernels along the modality dimension and its values divided by M in addition to being divided by the depth of the additional dimension.

At 1514, process 1500 can receive and pre-process unlabeled medical image data. For example, process 1500 can receive unlabeled T1 MRI scans and T2 MRI scans depicting the pancreas of a subject. In some embodiments, process 1500 can use any suitable technique or combination of techniques to pre-process the received unlabeled medical image data, such as techniques used to process the labeled medical image data at 1510. In some embodiments, process 1500 can receive any suitable number of slices corresponding to the subject's pancreas. For example, if the CNN has been trained to use five slices, process 1500 can receive five or more slices and can select five slices to use as input to the CNN. In such an example, the slices to be used as input can be automatically selected (e.g., without user input) based on a segmentation of the pancreas. Alternatively, the slices to be used as input can be semi-automatically selected (e.g., with at least some user input) based on a selection of a slide that includes the largest amount of pancreas and/or any other suitable criterion or criteria.

At 1516, process 1500 can provide the pre-processed unlabeled medical image data to the trained inflated IPMN classification CNN as input data.

At 1518, process 1500 can receive a classification of the unlabeled medical image data as output from the trained inflated IPMN classification CNN. For example, the output can be a set of values indicating a probability that the medical image data includes tissue corresponding to each class. In a more example, the output can be a tuple of values indicating a probability that the pancreas depicted in the MRI scans is normal, a probability that low grade IPMNs are present, and a probability that high grade IPMNs are present.

At 1520, process 1500 can present information (e.g., to a user) based on the classification. For example, process 1500 can cause a graphical user interface to present the most likely classification and a confidence in that classification. As another example, process 1500 can cause one or more of the input images to be presented in connection with information about a likely classification. As yet another example, process 1500 can cause a report indicating a likelihood that IPMNs of each class are present (or absent) to be presented (e.g., via a graphical user interface, via a printed report in an electronic or physical format).

FIG. 16 shows an example of a table of results comparing the precision, recall, and accuracy of a conventional technique for diagnosing IPMNs and various implementations of a system for automatically diagnosing IPMNs using multi-modal magnetic resonance imaging data in accordance with some embodiments of the disclosed subject matter. Images were split across three categories: normal (i.e., no IPMN was present), low-grade IPMN, and high-grade IPMN/invasive carcinoma. Whole-MRI experiments used 139 pairs of T1 and T2 scans, of which 29 were labeled normal, 45 were labeled low-grade, and 65 were labeled high-grade. Due to the extremely challenging nature of cropping the pancreas-ROI, two sets of crops were extracted by two different experts. In cases where at least one of the experts could not confidently extract a pancreas-ROI, this scan was skipped, yielding a total of 271 sets of pancreas-ROIs (i.e., seven sets of images were excluded due to disagreement over where in the images the pancreas was located). The results of several experiments are summarized in TABLE 5 shown in FIG. 16, which used the intermediate fusion strategy. For all experiments, the number of slices used was k=5, excluding experiments specifically examining the effect of k (e.g., as shown in TABLE 7 in FIG. 18). Unless otherwise specified, all experiments were conducted with stratified 10-fold cross-validation. A set of experiments was also conducted across one training fold to determine the relative performance of the early and intermediate fusion techniques, which is shown in TABLE 6 in FIG. 17. Note, experiments were not performed with DenseINN for whole-MRI due to memory constraints. Whole-MRI images were resized in-plane to 256×256 pixels per slice, and pancreas-ROIs were resized to 128×128 pixels per slice.

All training and testing was performed using Keras with TensorFlow on a single Titan-X GPU with 12 Gb of memory. The Adam optimizer was used with its default parameters, early stopping, and learning rate reduction by 0.05 on loss plateau. At training, input batches were formed by first sliding through each set of k slices containing the pancreas in a given scan, before moving on to the next scan. At testing, k slices were chosen around a central slice, where this slice was determined as the one in which the pancreas appears the largest. For pancreas-ROI images, a batch size of 32 was used for both networks. Due to memory limitations, InceptINN used a batch size of 16 when using the whole-MRI.

FIG. 17 shows an example of a table of results comparing the precision, recall, and accuracy of various implementations of a system for automatically diagnosing IPMNs using multi-modal magnetic resonance imaging data using different fusion strategies in accordance with some embodiments of the disclosed subject matter.

FIG. 18 shows an example of a table of results comparing the precision, recall, and accuracy of a system for automatically diagnosing IPMNs using multi-modal MRI data using different regions of interest and different numbers of MRI slices in accordance with some embodiments of the disclosed subject matter.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as RAM, Flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

It should be noted that, as used herein, the term mechanism can encompass hardware, software, firmware, or any suitable combination thereof.

It should be understood that the above described steps of the processes of FIGS. 4 and 5 can be executed or performed in any order or sequence not limited to the order and sequence shown and described in the figures. Also, some of the above steps of the processes of FIGS. 4 and 5 can be executed or performed substantially simultaneously where appropriate or in parallel to reduce latency and processing times.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways.

What is claimed is:

1. A system for automatically detecting the presence of intraductal papillary mucinous neoplasms (IPMNs) in a subject's pancreas, the system comprising:
    at least one hardware processor that is programmed to:
        receive T1 MRI data generated by an MRI machine, the T1 MRI data comprising a plurality of slices of T1 MRI data $[I_1, \ldots, I_u, \ldots, I_{N_1}]$;
        receive T2 MRI data generated by the MRI machine, the T2 MRI data comprising a plurality of slices of T2 MRI data $[J_1, \ldots, J_v, \ldots, J_{N_2}]$
        provide data representing k slices of the T1 MRI data to a trained image classification convolutional neural network (CNN);
        provide data representing k slices of the T2 MRI data to the trained image classification CNN;
        receive output from the trained image classification CNN;
        determine, based on the output, that IPMNs are likely present in the subject's pancreas;

in response to determining that IPMNs are likely present in the subject's pancreas, cause an indication that IPMNs are likely present in the subject's pancreas to be presented to the user.

2. The system of claim 1, further comprising the MRI scanner.

3. The system of claim 1, wherein the at least one hardware processor that is further programmed to:
present the T1 MRI data and prompt a user to select a slice of T1 MRI data including the subject's pancreas; and
receive a selection of slice $I_u$ the T1 MRI data.

4. The system of claim 1, wherein the at least one hardware processor is further programmed to:
generate a minimum intensity projection based on consecutive slices $[I_{u-m}, \ldots, I_u, \ldots, I_{u+m}]$ where m is greater than or equal to 2, and the data representing the k slices of the T1 MRI data comprises the minimum intensity projection;
generate a maximum intensity projection based on consecutive slices $[J_{v-m}, \ldots, J_v, \ldots, J_{v+m}]$ where m is greater than or equal to 2, and the data representing the k slices of the T2 MRI data comprises the maximum intensity projection;
provide the minimum intensity projection to the image classification CNN;
receive, from a fully connected layer of the image classification CNN, the output comprising a set of features $\Phi$ generated by the image classification CNN based on the minimum intensity projection;
provide the maximum intensity projection to the CNN;
receive, from the fully connected layer of the image classification CNN, a set of features $\Psi$ generated by the image classification CNN based on the maximum intensity projection;
calculate a feature matrix based on a canonical correlation analysis (CCA) between features $\Phi$ and features $\Psi$;
provide the feature matrix as input to a support vector machine (SVM) trained to automatically detect the presence of IPMNs in multi-modal MRI data corresponding to an imaged pancreas based on an input feature matrix generated from T1 and T2 MRI data corresponding to the imaged pancreas;
receive an output from the SVM that is indicative of the presence of IPMNs in slice $I_u$ and slice $J_v$; and
determine, based on the output from the SVM, that IPMNs are likely present in the subject's pancreas.

5. The system of claim 1, wherein the at least one hardware processor is further programmed to:
provide the k slices of the T1 MRI data to the trained image classification CNN, wherein the trained image classification CNN was generated using transfer learning to retrain at least one layer of a 3D image classification CNN that was expanded from a pre-trained general image classification CNN having a 2D architecture, the data representing the k slices of the T1 MRI data comprising the k slices of the T1 MRI data, and the weights of a plurality of kernels of the trained classification CNN are divided at least by a number of depth layers d added to the 2D architecture that is equal to k;
provide the k slices of the T2 MRI data to the trained image classification CNN; and
receive the output from the trained image classification CNN.

6. The system of claim 5, wherein the at least one hardware processor is further programmed to:

concatenate the T1 MRI data and the T2 MRI data prior to providing the T2 MRI data and the T2 MRI data to the trained image classification CNN.

7. The system of claim 5, wherein the at least one hardware processor is further programmed to:
provide the k slices of the T1 MRI data to a first convolutional layer of the trained image classification CNN;
provide the k slices of the T2 MRI data to a second convolutional layer of the trained image classification CNN;
concatenate an output of the first convolutional layer and an output of the second convolution layer; and
provide a set of features based on the concatenated outputs to a third convolutional layer.

8. A method for automatically detecting the presence of intraductal papillary mucinous neoplasms (IPMNs) in a subject's pancreas, the method comprising:
receiving T1 MRI data generated by an MRI machine, the T1 MRI data comprising a plurality of slices of T1 MRI data $[I_1, \ldots, I_u, \ldots, I_{N_1}]$;
receiving T2 MRI data generated by the MRI machine, the T2 MRI data comprising a plurality of slices of T2 MRI data $[J_1, \ldots, J_v, \ldots, J_{N_2}]$;
providing data representing k slices of the T1 MRI data to a trained image classification convolutional neural network (CNN);
providing data representing k slices of the T2 MRI data to the trained image classification CNN;
receiving output from the trained image classification CNN;
determining, based on the output, that IPMNs are likely present in the subject's pancreas; and
in response to determining that IPMNs are likely present in the subject's pancreas, causing an indication that IPMNs are likely present in the subject's pancreas to be presented to the user.

9. The method of claim 8, further comprising:
presenting the T1 MRI data and prompt a user to select a slice of T1 MRI data including the subject's pancreas; and
receiving a selection of slice $I_u$ of the T1 MRI data.

10. The method of claim 8, further comprising:
generating a minimum intensity projection based on consecutive slices $[I_{u-m}, \ldots, I_u, \ldots, I_{u+m}]$ where m is greater than or equal to 2, and the data representing the k slices of the T1 MRI data comprises the minimum intensity projection;
generating a maximum intensity projection based on consecutive slices $[J_{v-m}, \ldots, J_v, \ldots, J_{v+m}]$ where m is greater than or equal to 2, and the data representing the k slices of the T2 MRI data comprises the maximum intensity projection;
providing the minimum intensity projection to the image classification CNN;
receiving, from a fully connected layer of the image classification CNN, the output comprising a set of features $\Phi$ generated by the image classification CNN based on the minimum intensity projection;
providing the maximum intensity projection to the CNN;
receiving, from the fully connected layer of the image classification CNN, a set of features $\Psi$ generated by the image classification CNN based on the maximum intensity projection;
calculating a feature matrix based on a canonical correlation analysis (CCA) between features $\Phi$ and features $\Psi$;

providing the feature matrix as input to a support vector machine (SVM) trained to automatically detect the presence of IPMNs in multi-modal MRI data corresponding to an imaged pancreas based on an input feature matrix generated from T1 and T2 MRI data corresponding to the imaged pancreas;

receiving an output from the SVM that is indicative of the presence of IPMNs in slice $I_u$ and slice $J_v$; and determining, based on the output from the SVM, that IPMNs are likely present in the subject's pancreas.

11. The method of claim 8, further comprising:

providing the k slices of the T1 MRI data to the trained image classification CNN, wherein the trained image classification CNN was generated using transfer learning to retrain at least one layer of a 3D image classification CNN that was expanded from a pre-trained general image classification CNN having a 2D architecture, the data representing the k slices of the T1 MRI data comprising the k slices of the T1 MRI data, and the weights of a plurality of kernels of the trained classification CNN are divided at least by a number of depth layers d added to the 2D architecture that is equal to k;

providing the k slices of the T2 MRI data to the trained image classification CNN; and receiving the output from the trained image classification CNN.

12. The method of claim 11, further comprising:

concatenating the T1 MRI data and the T2 MRI data prior to providing the T1 MRI data and the T2 MRI data to the trained image classification CNN.

13. The method of claim 11, further comprising:

providing the k slices of the T1 MRI data to a first convolutional layer of the trained image classification CNN;

provide the k slices of the T2 MRI data to a second convolutional layer of the trained image classification CNN;

concatenate an output of the first convolutional layer and an output of the second convolution layer; and provide a set of features based on the concatenated outputs to a third convolutional layer.

14. A non-transitory computer readable medium containing computer executable instructions that, when executed by a processor, cause the processor to perform a method for automatically detecting the presence of intraductal papillary mucinous neoplasms (IPMNs) in a subject's pancreas, the method comprising:

receiving T1 MRI data generated by an MRI machine, the T1 MRI data comprising a plurality of slices of T1 MRI data $[I_1, \ldots, I_u, \ldots, I_{N_1}]$;

receiving T2 MRI data generated by the MRI machine, the T2 MRI data comprising a plurality of slices of T2 MRI data $[J_1, \ldots, J_v, \ldots, J_{N_2}]$;

providing data representing k slices of the T1 MRI data to a trained image classification convolutional neural network (CNN);

providing data representing k slices of the T2 MRI data to the trained image classification CNN;

receiving output from the trained image classification CNN;

determining, based on the output, that IPMNs are likely present in the subject's pancreas; and in response to determining that IPMNs are likely present in the subject's pancreas, causing an indication that IPMNs are likely present in the subject's pancreas to be presented to the user.

15. The non-transitory computer readable medium of claim 14, wherein the method further comprises:

presenting the T1 MRI data and prompt a user to select a slice of T1 MRI data including the subject's pancreas; and receiving a selection of slice $I_u$ of the T1 MRI data.

16. The non-transitory computer readable medium of claim 14, wherein the method further comprises:

generating a minimum intensity projection based on consecutive slices $[I_{u-m}, \ldots, I_u, \ldots, I_{u+m}]$ where m is greater than or equal to 2, and the data representing the k slices of the T1 MRI data comprises the minimum intensity projection;

generating a maximum intensity projection based on consecutive slices $[J_{v-m}, \ldots, J_v, \ldots, J_{v+m}]$ where m is greater than or equal to 2, and the data representing the k slices of the T2 MRI data comprises the maximum intensity projection;

providing the minimum intensity projection to the image classification CNN;

receiving, from a fully connected layer of the image classification CNN, the output comprising a set of features $\Phi$ generated by the image classification CNN based on the minimum intensity projection;

providing the maximum intensity projection to the CNN;

receiving, from the fully connected layer of the image classification CNN, a set of features $\Psi$ generated by the image classification CNN based on the maximum intensity projection;

calculating a feature matrix based on a canonical correlation analysis (CCA) between features $\Phi$ and features $\Psi$;

providing the feature matrix as input to a support vector machine (SVM) trained to automatically detect the presence of IPMNs in multi-modal MRI data corresponding to an imaged pancreas based on an input feature matrix generated from T1 and T2 MRI data corresponding to the imaged pancreas;

receiving an output from the SVM that is indicative of the presence of IPMNs in slice $I_u$ and slice $J_v$; and determining, based on the output from the SVM, that IPMNs are likely present in the subject's pancreas.

17. The non-transitory computer readable medium of claim 14, wherein the method further comprises:

providing the k slices of the T1 MRI data to the trained image classification CNN, wherein the trained image classification CNN was generated using transfer learning to retrain at least one layer of a 3D image classification CNN that was expanded from a pre-trained general image classification CNN having a 2D architecture, the data representing the k slices of the T1 MRI data comprising the k slices of the T1 MRI data, and the weights of a plurality of kernels of the trained classification CNN are divided at least by a number of depth layers d added to the 2D architecture that is equal to k;

providing the k slices of the T2 MRI data to the trained image classification CNN; and receiving the output from the trained image classification CNN.

18. The non-transitory computer readable medium of claim 17, wherein the method further comprises:

concatenating the T1 MRI data and the T2 MRI data prior to providing the T1 MRI data and the T2 MRI data to the trained image classification CNN.

19. The non-transitory computer readable medium of claim 17, wherein the method further comprises:

providing the k slices of the T1 MRI data to a first convolutional layer of the trained image classification CNN;
provide the k slices of the T2 MRI data to a second convolutional layer of the trained image classification CNN;
concatenate an output of the first convolutional layer and an output of the second convolution layer; and
provide a set of features based on the concatenated outputs to a third convolutional layer.

* * * * *

UNITED STATES PATENT AND TRADEMARK OFFICE
CERTIFICATE OF CORRECTION

PATENT NO. : 11,064,902 B2  
APPLICATION NO. : 16/459437  
DATED : July 20, 2021  
INVENTOR(S) : Michael B. Wallace et al.

Page 1 of 1

It is certified that error appears in the above-identified patent and that said Letters Patent is hereby corrected as shown below:

In the Specification

Column 1, Lines 14-19, should be deleted.

Column 12, Line 54, "$l_2$" should be -- $\ell_2$ --.

Column 13, Line 5, "$C_{\Phi\Psi} = C_{\Phi\Psi}{}^T$" should be -- $C_{\Phi\Psi} = C_{\Phi\Psi}^T$ --.

Column 13, Line 14, "$\Phi^* = W_\Phi{}^T\Phi$ and $\Psi * W_\Psi{}^T\Psi$" should be -- $\Phi^* = W_\Phi^T\Phi$ and $\Psi * W_\Psi^T\Psi$ --.

Column 13, Line 20, Eq. (3), "$\mathrm{corr}(\Theta^*, \Psi^*) = \frac{\mathrm{cov}(\Phi^*, \Psi^*)}{\mathrm{var}(\Phi^*) \cdot \mathrm{var}(\Psi^*)}$" should be -- $\mathrm{corr}(\Phi^*, \Psi^*) = \frac{\mathrm{cov}(\Phi^*, \Psi^*)}{\mathrm{var}(\Phi^*) \cdot \mathrm{var}(\Psi^*)}$ --.

Column 13, Line 23, "$\mathrm{cov}(\Phi^*, \Psi^*) = W_\Phi{}^T C_{\Phi\Psi} W_\Psi, \mathrm{var}(\Phi^*) = W_\Phi{}^T C_{\Phi\Phi} W_\Phi$" should be -- $\mathrm{cov}(\Phi^*, \Psi^*) = W_\Phi^T C_{\Phi\Psi} W_\Psi, \mathrm{var}(\Phi^*) = W_\Phi^T C_{\Phi\Phi} W_\Phi$ --.

Column 13, Line 24, "$\mathrm{var}(\Psi^*) = W_\Psi{}^T C_{\Psi\Psi} W_\Psi$" should be -- $\mathrm{var}(\Psi^*) = W_\Psi^T C_{\Psi\Psi} W_\Psi$ --.

Column 13, Eq. (4), "$C_{\Phi\Phi}{}^{-1} C_{\Phi\Psi} C_{\Psi\Psi}{}^{-1} C_{\Psi\Phi} \tilde{W}_\Phi = \Lambda^2 \tilde{W}_\Phi$, $C_{\Psi\Psi}{}^{-1} C_{\Psi\Phi} C_{\Phi\Phi}{}^{-1} C_{\Phi\Psi} \tilde{W}_\Psi = \Lambda^2 \tilde{W}_\Psi$," should be -- $C_{\Phi\Phi}^{-1} C_{\Phi\Psi} C_{\Psi\Psi}^{-1} C_{\Psi\Phi} \tilde{W}_\Phi = \Lambda^2 \tilde{W}_\Phi$, $C_{\Psi\Psi}^{-1} C_{\Psi\Phi} C_{\Phi\Phi}^{-1} C_{\Phi\Psi} \tilde{W}_\Psi = \Lambda^2 \tilde{W}_\Psi$, --.

Signed and Sealed this  
Fourteenth Day of September, 2021

Drew Hirshfeld  
*Performing the Functions and Duties of the*  
*Under Secretary of Commerce for Intellectual Property and*  
*Director of the United States Patent and Trademark Office*